United States Patent
Blanquart et al.

(10) Patent No.: US 10,980,406 B2
(45) Date of Patent: Apr. 20, 2021

(54) IMAGE SENSOR SYNCHRONIZATION WITHOUT INPUT CLOCK AND DATA TRANSMISSION CLOCK

(71) Applicant: DePuy Synthes Products, Inc., Raynham, MA (US)

(72) Inventors: Laurent Blanquart, Westlake Village, CA (US); Donald M. Wichern, Ogden, UT (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

(21) Appl. No.: 16/730,737

(22) Filed: Dec. 30, 2019

(65) Prior Publication Data
US 2020/0138279 A1    May 7, 2020

Related U.S. Application Data

(63) Continuation of application No. 14/214,790, filed on Mar. 15, 2014, now Pat. No. 10,517,469.

(60) Provisional application No. 61/790,590, filed on Mar. 15, 2013, provisional application No. 61/800,502, filed on Mar. 15, 2013.

(51) Int. Cl.
| | |
|---|---|
| *H04N 5/376* | (2011.01) |
| *A61B 1/045* | (2006.01) |
| *A61B 1/05* | (2006.01) |
| *A61B 1/06* | (2006.01) |
| *H04N 5/225* | (2006.01) |

(52) U.S. Cl.
CPC .......... *A61B 1/045* (2013.01); *A61B 1/05* (2013.01); *A61B 1/0638* (2013.01); *H04N 5/3765* (2013.01); *H04N 2005/2255* (2013.01)

(58) Field of Classification Search
CPC ................ H04N 2005/2255; H04N 5/3765
See application file for complete search history.

(56) References Cited

U.S. PATENT DOCUMENTS

| | | |
|---|---|---|
| 3,796,220 A | 3/1974 | Bredemeier |
| 3,858,577 A | 1/1975 | Bass et al. |
| 4,011,403 A | 3/1977 | Epstein et al. |
| 4,153,356 A | 5/1979 | Hama |
| 4,350,150 A | 9/1982 | Kubota et al. |
| 4,363,963 A | 12/1982 | Ando |
| 4,429,686 A | 2/1984 | Hosoda |
| 4,433,675 A | 2/1984 | Konoshima |
| 4,436,095 A | 3/1984 | Kruger |

(Continued)

FOREIGN PATENT DOCUMENTS

| | | |
|---|---|---|
| AU | 2012253253 B2 | 11/2012 |
| AU | 2012253261 | 6/2016 |

(Continued)

OTHER PUBLICATIONS

H.Kurino et al., Intelligent image sensor chip with three dimensional structure, Technical Digest, International Electron Devices Meeting 1999, Dec. 5, 1999, pp. 879-882.

*Primary Examiner* — Jamie J Atala
*Assistant Examiner* — Hesham K Abouzahra
(74) *Attorney, Agent, or Firm* — Terrence J. Edwards; TechLaw Ventures, PLLC

(57) ABSTRACT

The disclosure extends to systems and methods for reducing the area of an image sensor by reducing the imaging sensor pad count used for data transmission and clock generation.

24 Claims, 16 Drawing Sheets

(56) References Cited

U.S. PATENT DOCUMENTS

| | | |
|---|---|---|
| 4,561,430 A | 12/1985 | Walsh |
| 4,572,164 A | 2/1986 | Yoshida et al. |
| 4,589,404 A | 5/1986 | Barath et al. |
| 4,600,940 A | 7/1986 | Sluyter |
| 4,604,992 A | 8/1986 | Sato |
| 4,670,653 A | 6/1987 | McConkie et al. |
| 4,740,837 A | 4/1988 | Yanagisawa et al. |
| 4,741,327 A | 5/1988 | Yabe |
| 4,745,471 A | 5/1988 | Takamura et al. |
| 4,773,396 A | 9/1988 | Okazaki |
| 4,786,965 A | 11/1988 | Yabe |
| 4,800,424 A | 1/1989 | Noguchi |
| 4,831,444 A | 5/1989 | Kato |
| 4,832,003 A | 5/1989 | Yabe |
| 4,845,555 A | 7/1989 | Yabe et al. |
| 4,853,772 A | 8/1989 | Kikuchi |
| 4,866,526 A | 9/1989 | Ams et al. |
| 4,888,639 A | 12/1989 | Yabe et al. |
| 4,918,521 A | 4/1990 | Yabe et al. |
| 4,938,205 A | 7/1990 | Nudelman |
| 4,942,473 A | 7/1990 | Zeevi et al. |
| 4,953,539 A | 9/1990 | Nakamura et al. |
| 4,954,878 A | 9/1990 | Fox et al. |
| 5,010,038 A | 4/1991 | Fox et al. |
| 5,010,876 A | 4/1991 | Henley et al. |
| 5,016,975 A | 5/1991 | Sasaki et al. |
| 5,021,888 A | 6/1991 | Kondou et al. |
| 5,042,915 A | 8/1991 | Akutsu et al. |
| 5,065,444 A | 11/1991 | Garber |
| RE33,854 E | 3/1992 | Adair |
| 5,103,497 A | 4/1992 | Hicks |
| 5,111,804 A | 5/1992 | Funakoshi |
| 5,115,309 A | 5/1992 | Hang |
| 5,133,035 A | 7/1992 | Hicks |
| 5,168,361 A | 12/1992 | Hackmann |
| 5,168,863 A | 12/1992 | Kurtzer |
| 5,187,572 A | 2/1993 | Nakamura et al. |
| 5,188,094 A | 2/1993 | Adair |
| 5,196,938 A | 3/1993 | Blessinger |
| 5,200,838 A | 4/1993 | Nudelman et al. |
| 5,220,198 A | 6/1993 | Tsuji |
| 5,227,662 A | 7/1993 | Ohno et al. |
| 5,228,430 A | 7/1993 | Sakamoto |
| 5,237,403 A | 8/1993 | Sugimoto et al. |
| 5,241,170 A | 8/1993 | Field, Jr. et al. |
| 5,277,172 A | 1/1994 | Sugimoto |
| 5,289,555 A | 2/1994 | Sanso |
| 5,307,804 A | 5/1994 | Bonnet |
| 5,313,306 A | 5/1994 | Kuban et al. |
| 5,325,847 A | 7/1994 | Matsuno |
| 5,339,275 A | 8/1994 | Hyatt |
| 5,381,784 A | 1/1995 | Adair |
| 5,400,267 A | 3/1995 | Denen et al. |
| 5,402,768 A | 4/1995 | Adair |
| 5,411,020 A | 5/1995 | Ito |
| 5,427,087 A | 6/1995 | Ito et al. |
| 5,454,366 A | 10/1995 | Ito et al. |
| 5,461,425 A | 10/1995 | Fowler et al. |
| 5,471,515 A | 11/1995 | Fossum et al. |
| 5,489,801 A | 2/1996 | Blish, II |
| 5,494,483 A | 2/1996 | Adair |
| 5,522,006 A | 5/1996 | Takeuchi et al. |
| 5,523,786 A | 6/1996 | Parulski |
| 5,550,595 A | 8/1996 | Hannah |
| 5,576,781 A | 11/1996 | Deleeuw |
| 5,594,282 A | 1/1997 | Otsuki |
| 5,594,497 A | 1/1997 | Ahem et al. |
| 5,614,763 A | 3/1997 | Womack |
| 5,665,959 A | 9/1997 | Fossum et al. |
| 5,721,422 A | 2/1998 | Bird |
| 5,734,418 A | 3/1998 | Danna |
| 5,748,234 A | 5/1998 | Lippincott |
| 5,754,313 A | 5/1998 | Pelchy et al. |
| 5,757,075 A | 5/1998 | Kitaoka |
| 5,784,099 A | 7/1998 | Lippincott |
| 5,787,298 A | 7/1998 | Broedner et al. |
| 5,841,126 A | 11/1998 | Fossum et al. |
| 5,857,963 A | 1/1999 | Pelchy et al. |
| 5,879,289 A | 3/1999 | Yarush et al. |
| 5,887,049 A | 3/1999 | Fossum |
| 5,896,166 A | 4/1999 | D'Alfonso et al. |
| 5,907,178 A | 5/1999 | Baker et al. |
| 5,929,901 A | 7/1999 | Adair et al. |
| 5,949,483 A | 9/1999 | Fossum et al. |
| 5,986,693 A | 11/1999 | Adair et al. |
| 5,990,506 A | 11/1999 | Fossum et al. |
| 6,005,619 A | 12/1999 | Fossum |
| 6,021,172 A | 2/2000 | Fossum et al. |
| 6,023,315 A | 2/2000 | Harrold et al. |
| 6,027,955 A | 2/2000 | Lee et al. |
| 6,028,330 A | 2/2000 | Lee et al. |
| 6,043,839 A | 3/2000 | Adair et al. |
| 6,059,776 A | 5/2000 | Gatto |
| 6,059,793 A | 5/2000 | Pagedas |
| 6,073,043 A | 6/2000 | Schneider |
| 6,096,573 A | 8/2000 | Chen |
| 6,101,232 A | 8/2000 | Fossum et al. |
| 6,118,142 A | 9/2000 | Chen et al. |
| 6,139,489 A | 10/2000 | Wampler et al. |
| 6,142,930 A | 11/2000 | Ito et al. |
| 6,144,542 A | 11/2000 | Ker et al. |
| 6,166,367 A | 12/2000 | Cho |
| 6,166,768 A | 12/2000 | Fossum et al. |
| 6,180,969 B1 | 1/2001 | Yang et al. |
| 6,184,055 B1 | 2/2001 | Yang et al. |
| 6,194,260 B1 | 2/2001 | Chien et al. |
| 6,198,087 B1 | 3/2001 | Boon |
| 6,207,984 B1 | 3/2001 | Chang |
| 6,211,904 B1 | 4/2001 | Adair et al. |
| 6,215,517 B1 | 4/2001 | Takahashi et al. |
| 6,239,456 B1 | 5/2001 | Berezin et al. |
| 6,242,277 B1 | 6/2001 | Lin et al. |
| 6,255,681 B1 | 7/2001 | Pan |
| 6,272,269 B1 | 8/2001 | Naum |
| 6,275,255 B1 | 8/2001 | Adair et al. |
| 6,294,775 B1 | 9/2001 | Seibel et al. |
| 6,303,421 B1 | 10/2001 | Chang |
| 6,310,642 B1 | 10/2001 | Adair et al. |
| 6,313,868 B1 | 11/2001 | D'Alfonso et al. |
| 6,320,630 B1 | 11/2001 | Yamashita et al. |
| 6,327,493 B1 | 12/2001 | Ozawa et al. |
| 6,331,156 B1 | 12/2001 | Haefele et al. |
| 6,333,205 B1 | 12/2001 | Rhodes |
| 6,369,812 B1 | 4/2002 | Iyriboz et al. |
| 6,387,043 B1 | 5/2002 | Yoon |
| 6,388,243 B1 | 5/2002 | Berezin et al. |
| 6,389,205 B1 | 5/2002 | Muckner et al. |
| 6,390,972 B1 | 5/2002 | Speier et al. |
| 6,400,824 B1 | 6/2002 | Mansoorian et al. |
| 6,404,048 B2 | 6/2002 | Akram |
| 6,410,377 B1 | 6/2002 | Hwang et al. |
| 6,416,463 B1 | 7/2002 | Tsuzuki et al. |
| 6,419,626 B1 | 7/2002 | Yoon |
| 6,419,627 B1 | 7/2002 | Ben Nun |
| 6,424,369 B1 | 7/2002 | Adair et al. |
| 6,436,032 B1 | 8/2002 | Eto et al. |
| 6,441,482 B1 | 8/2002 | Foster |
| 6,452,626 B1 | 9/2002 | Adair et al. |
| 6,456,326 B2 | 9/2002 | Fossum et al. |
| 6,469,739 B1 | 10/2002 | Bechtel et al. |
| 6,485,414 B1 | 11/2002 | Neuberger |
| 6,512,280 B2 | 1/2003 | Chen et al. |
| 6,515,321 B1 | 2/2003 | Jwo |
| 6,549,235 B1 | 4/2003 | Fossum et al. |
| 6,555,842 B1 | 4/2003 | Fossum et al. |
| 6,570,617 B2 | 5/2003 | Fossum et al. |
| 6,588,884 B1 | 7/2003 | Furlani et al. |
| 6,606,122 B1 | 8/2003 | Shaw et al. |
| 6,610,557 B2 | 8/2003 | Lee et al. |
| 6,627,474 B2 | 9/2003 | Barna et al. |
| 6,659,940 B2 | 12/2003 | Adler |
| 6,665,013 B1 | 12/2003 | Fossum et al. |
| 6,690,466 B2 | 2/2004 | Miller et al. |
| 6,692,431 B2 | 2/2004 | Kazakevich |

(56) References Cited

U.S. PATENT DOCUMENTS

| | | |
|---|---|---|
| 6,704,049 B1 | 3/2004 | Fossum |
| 6,720,810 B1 | 4/2004 | New |
| 6,726,620 B2 | 4/2004 | Shibata et al. |
| 6,730,900 B2 | 5/2004 | Hsish et al. |
| 6,740,870 B1 | 5/2004 | Doudoumopoulos |
| 6,744,068 B2 | 6/2004 | Fossum et al. |
| 6,773,392 B2 | 8/2004 | Kikuchi et al. |
| 6,784,940 B1 | 8/2004 | Takazawa et al. |
| 6,796,939 B1 | 9/2004 | Hirata et al. |
| 6,799,065 B1 | 9/2004 | Niemeyer |
| 6,809,358 B2 | 10/2004 | Hsieh et al. |
| 6,812,949 B1 | 11/2004 | Switzer et al. |
| 6,838,653 B2 | 1/2005 | Campbell et al. |
| 6,838,716 B2 | 1/2005 | Asada et al. |
| 6,856,712 B2 | 1/2005 | Fauver et al. |
| 6,862,036 B2 | 3/2005 | Adair et al. |
| 6,879,340 B1 | 4/2005 | Chevallier |
| 6,897,082 B2 | 5/2005 | Rhodes et al. |
| 6,899,675 B2 | 5/2005 | Cline et al. |
| 6,921,920 B2 | 7/2005 | Kazakevich |
| 6,943,838 B2 | 9/2005 | Fossum et al. |
| 6,947,090 B2 | 9/2005 | Komoro et al. |
| 6,961,461 B2 | 11/2005 | MacKinnon et al. |
| 6,970,195 B1 | 11/2005 | Bidermann et al. |
| 6,976,954 B2 | 12/2005 | Takahashi |
| 6,977,733 B2 | 12/2005 | Denk et al. |
| 6,982,740 B2 | 1/2006 | Adair et al. |
| 6,982,742 B2 | 1/2006 | Adair et al. |
| 6,997,871 B2 | 2/2006 | Sonnenschein et al. |
| 6,999,118 B2 | 2/2006 | Suzuki |
| 7,002,231 B2 | 2/2006 | Rhodes et al. |
| 7,002,621 B2 | 2/2006 | Adair et al. |
| 7,009,634 B2 | 3/2006 | Iddan et al. |
| 7,009,646 B1 | 3/2006 | Fossum et al. |
| 7,018,331 B2 | 3/2006 | Chang et al. |
| 7,027,092 B2 | 4/2006 | Altree |
| 7,030,904 B2 | 4/2006 | Adair et al. |
| 7,037,259 B2 | 5/2006 | Hakamata et al. |
| 7,061,117 B2 | 6/2006 | Yang et al. |
| 7,068,878 B2 | 6/2006 | Crossman-Bosworth et al. |
| 7,070,560 B2 | 7/2006 | Takahashi |
| 7,071,979 B1 | 7/2006 | Ohtani et al. |
| 7,088,398 B1 | 8/2006 | Wolf et al. |
| 7,102,682 B2 | 9/2006 | Baer |
| 7,105,371 B2 | 9/2006 | Fossum et al. |
| 7,106,367 B2 | 9/2006 | Sarwari |
| 7,106,377 B2 | 9/2006 | Bean et al. |
| 7,115,091 B2 | 10/2006 | Root et al. |
| 7,129,108 B2 | 10/2006 | Jang |
| 7,151,568 B2 | 12/2006 | Kawachi et al. |
| 7,183,129 B2 | 2/2007 | Lee |
| 7,184,084 B2 | 2/2007 | Glenn |
| 7,189,226 B2 | 3/2007 | Auld et al. |
| 7,193,519 B2 | 3/2007 | Root et al. |
| 7,202,899 B2 | 4/2007 | Lin et al. |
| 7,217,967 B2 | 5/2007 | Han |
| 7,227,469 B2 | 6/2007 | Varner et al. |
| 7,230,247 B2 | 6/2007 | Shibayama |
| 7,230,615 B2 | 6/2007 | Wang et al. |
| 7,232,712 B2 | 6/2007 | Han |
| 7,244,920 B2 | 7/2007 | Kim et al. |
| 7,250,594 B2 | 7/2007 | Lin et al. |
| 7,258,546 B2 | 8/2007 | Beier et al. |
| 7,258,663 B2 | 8/2007 | Doguchi et al. |
| 7,261,687 B2 | 8/2007 | Yang |
| 7,273,452 B2 | 9/2007 | Barbato et al. |
| 7,274,390 B2 | 9/2007 | Sevat et al. |
| 7,276,785 B2 | 10/2007 | Bauer et al. |
| 7,280,139 B2 | 10/2007 | Pahr et al. |
| 7,282,025 B2 | 10/2007 | Abe |
| 7,283,566 B2 | 10/2007 | Siemens et al. |
| 7,295,578 B1 | 11/2007 | Lyle et al. |
| 7,303,528 B2 | 11/2007 | Johnston |
| 7,317,955 B2 | 1/2008 | McGreevy |
| 7,319,478 B2 | 1/2008 | Dolt et al. |
| 7,331,523 B2 | 2/2008 | Meier et al. |
| 7,338,832 B2 | 3/2008 | Park et al. |
| 7,339,982 B2 | 3/2008 | Wood, Jr. |
| 7,354,841 B2 | 4/2008 | Jeon |
| 7,365,768 B1 | 4/2008 | Ono et al. |
| 7,368,771 B2 | 5/2008 | Roh et al. |
| 7,369,166 B2 | 5/2008 | Fossum et al. |
| 7,369,176 B2 | 5/2008 | Sonnenschein et al. |
| 7,386,084 B2 | 6/2008 | Yin |
| 7,391,013 B2 | 6/2008 | Johnston et al. |
| 7,397,076 B2 | 7/2008 | Jang |
| 7,402,811 B2 | 7/2008 | Hatanaka et al. |
| 7,443,296 B2 | 10/2008 | Mezhinsky et al. |
| 7,470,893 B2 | 12/2008 | Suzuki et al. |
| 7,488,637 B2 | 2/2009 | Kim |
| 7,511,257 B2 | 3/2009 | Lee et al. |
| 7,517,351 B2 | 4/2009 | Culp et al. |
| 7,522,341 B2 | 4/2009 | Mouli |
| 7,525,168 B2 | 4/2009 | Hsieh |
| 7,534,645 B2 | 5/2009 | Choi |
| 7,535,037 B2 | 5/2009 | Lyu |
| 7,540,645 B2 | 6/2009 | Kazakevich |
| 7,542,069 B2 | 6/2009 | Tashiro |
| 7,544,163 B2 | 6/2009 | MacKinnon et al. |
| 7,545,434 B2 | 6/2009 | Bean et al. |
| 7,551,059 B2 | 6/2009 | Farrier |
| 7,564,935 B2 | 7/2009 | Suzuki |
| 7,567,291 B2 | 7/2009 | Bechtel et al. |
| 7,568,619 B2 | 8/2009 | Todd et al. |
| 7,573,516 B2 | 8/2009 | Krymski et al. |
| 7,578,786 B2 | 8/2009 | Boulais et al. |
| 7,583,872 B2 | 9/2009 | Seibel et al. |
| 7,589,349 B2 | 9/2009 | Hong |
| 7,595,210 B2 | 9/2009 | Shim |
| 7,598,686 B2 | 10/2009 | Lys et al. |
| 7,599,439 B2 | 10/2009 | Lavelle et al. |
| 7,605,016 B2 | 10/2009 | Min |
| 7,608,874 B2 | 10/2009 | Lee et al. |
| 7,612,318 B2 | 11/2009 | Jeon |
| 7,615,808 B2 | 11/2009 | Pain et al. |
| 7,615,838 B2 | 11/2009 | Kim |
| 7,616,986 B2 | 11/2009 | Seibel et al. |
| 7,630,008 B2 | 12/2009 | Sarwari |
| 7,646,407 B2 | 1/2010 | Fossum et al. |
| 7,663,115 B2 | 2/2010 | Korthout et al. |
| 7,744,528 B2 | 6/2010 | Wallace et al. |
| 7,749,799 B2 | 7/2010 | Pain |
| 7,768,562 B2 | 8/2010 | Boemler |
| 7,794,394 B2 | 9/2010 | Frangioni |
| 7,795,650 B2 | 9/2010 | Eminoglu et al. |
| 7,800,192 B2 | 9/2010 | Venezia et al. |
| 7,801,584 B2 | 9/2010 | Iddan et al. |
| 7,830,434 B2 | 11/2010 | Li et al. |
| 7,868,283 B2 | 1/2011 | Mabuchi |
| 7,871,373 B2 | 1/2011 | Yamada |
| 7,880,662 B2 | 2/2011 | Bogaerts |
| 7,901,974 B2 | 3/2011 | Venezia et al. |
| 7,914,447 B2 | 3/2011 | Kanai |
| 7,916,193 B2 | 3/2011 | Fossum |
| 7,923,763 B2 | 4/2011 | Lauxtermann |
| 7,935,050 B2 | 5/2011 | Launava et al. |
| 7,936,394 B2 | 5/2011 | Wu |
| 7,944,566 B2 | 5/2011 | Xie |
| 7,952,096 B2 | 5/2011 | Rhodes |
| 7,973,342 B2 | 7/2011 | Jeon |
| 7,995,123 B2 | 8/2011 | Lee et al. |
| 8,089,542 B2 | 1/2012 | Chevallier |
| 8,100,826 B2 | 1/2012 | MacKinnon et al. |
| 8,101,903 B2 | 1/2012 | Mokhnatyuk |
| 8,154,055 B2 | 4/2012 | Ha |
| 8,159,584 B2 | 4/2012 | Iwabuchi et al. |
| 8,193,542 B2 | 6/2012 | Machara |
| 8,212,884 B2 | 7/2012 | Seibel et al. |
| 8,300,111 B2 | 10/2012 | Iwane |
| 8,317,689 B1 | 11/2012 | Remijan et al. |
| 8,382,662 B2 | 2/2013 | Soper et al. |
| 8,384,814 B2 | 2/2013 | Chevallier |
| 8,396,535 B2 | 3/2013 | Wang et al. |
| 8,405,748 B2 | 3/2013 | Mao et al. |

(56) References Cited

U.S. PATENT DOCUMENTS

| | | |
|---|---|---|
| 8,423,110 B2 | 4/2013 | Barbato et al. |
| 8,426,096 B2 | 4/2013 | Maezawa |
| 8,471,938 B2 | 6/2013 | Altice, Jr. et al. |
| 8,476,575 B2 | 7/2013 | Mokhnatyuk |
| 8,493,474 B2 | 7/2013 | Richardson |
| 8,493,564 B2 | 7/2013 | Brukilacchio et al. |
| 8,523,367 B2 | 9/2013 | Ogura |
| 8,537,203 B2 | 9/2013 | Seibel et al. |
| 8,582,011 B2 | 11/2013 | Dosluoglu |
| 8,602,971 B2 | 12/2013 | Farr |
| 8,614,754 B2 | 12/2013 | Fossum |
| 8,625,016 B2 | 1/2014 | Fossum et al. |
| 8,629,023 B2 | 1/2014 | Lee |
| 8,638,847 B2 | 1/2014 | Wang |
| 8,648,287 B1 | 2/2014 | Fossum |
| 8,649,848 B2 | 2/2014 | Crane et al. |
| 8,668,339 B2 | 3/2014 | Kabuki et al. |
| 8,675,125 B2 | 3/2014 | Cossairt et al. |
| 8,698,887 B2 | 4/2014 | Makino et al. |
| 8,733,660 B2 | 5/2014 | Wang et al. |
| 8,754,358 B2 | 6/2014 | Chou et al. |
| 8,797,434 B2 | 8/2014 | Lee et al. |
| 8,830,340 B2 | 9/2014 | Burt et al. |
| 8,836,834 B2 | 9/2014 | Hashimoto et al. |
| 8,854,517 B2 | 10/2014 | Honda et al. |
| 8,858,425 B2 | 10/2014 | Farr et al. |
| 8,885,034 B2 | 11/2014 | Adair et al. |
| 8,896,730 B2 | 11/2014 | Fossum |
| 8,952,312 B2 | 2/2015 | Blanquart et al. |
| 9,066,677 B2 | 6/2015 | Seto |
| 9,123,602 B2 | 9/2015 | Blanquart |
| 9,153,609 B2 | 10/2015 | Blanquart |
| 9,343,489 B2 | 5/2016 | Blanquart et al. |
| 9,462,234 B2 | 10/2016 | Blanquart et al. |
| 9,763,566 B2 | 9/2017 | Blanquart |
| 9,907,459 B2 | 3/2018 | Blanquart |
| 10,517,469 B2 | 12/2019 | Blanquart et al. |
| 10,517,471 B2 | 12/2019 | Blanquart |
| 10,537,234 B2 | 1/2020 | Blanquart |
| 10,701,254 B2 | 6/2020 | Blanquart et al. |
| 10,709,319 B2 | 7/2020 | Blanquart |
| 10,750,933 B2 | 8/2020 | Blanquart |
| 2001/0016804 A1 | 8/2001 | Cunningham et al. |
| 2001/0019361 A1 | 9/2001 | Savoye |
| 2001/0030744 A1 | 10/2001 | Chang |
| 2001/0041825 A1 | 11/2001 | Shibata et al. |
| 2001/0052930 A1 | 12/2001 | Adair et al. |
| 2002/0011809 A1 | 1/2002 | Hartge et al. |
| 2002/0017611 A1 | 2/2002 | Tashiro et al. |
| 2002/0044207 A1 | 4/2002 | Dielhof et al. |
| 2002/0067408 A1 | 6/2002 | Adair et al. |
| 2002/0080248 A1 | 6/2002 | Adair et al. |
| 2002/0158986 A1 | 10/2002 | Baer |
| 2002/0163578 A1 | 11/2002 | Adair et al. |
| 2002/0180867 A1 | 12/2002 | Adair et al. |
| 2003/0007087 A1 | 1/2003 | Hakamata et al. |
| 2003/0007686 A1 | 1/2003 | Roever |
| 2003/0043264 A1 | 3/2003 | Furuya et al. |
| 2003/0052983 A1 | 3/2003 | Altree |
| 2003/0107664 A1 | 6/2003 | Suzuki |
| 2003/0146994 A1 | 8/2003 | Kokubun |
| 2003/0163029 A1 | 8/2003 | Sonnenschein et al. |
| 2003/0187586 A1 | 10/2003 | Katzenmaier et al. |
| 2003/0189663 A1 | 10/2003 | Dolt et al. |
| 2003/0218120 A1 | 11/2003 | Shibayama |
| 2004/0010196 A1 | 1/2004 | Wang et al. |
| 2004/0036010 A1 | 2/2004 | Hsieh et al. |
| 2004/0049215 A1 | 3/2004 | Snow et al. |
| 2004/0073086 A1 | 4/2004 | Abe |
| 2004/0078494 A1 | 4/2004 | Lennox et al. |
| 2004/0082833 A1 | 4/2004 | Adler et al. |
| 2004/0095495 A1 | 5/2004 | Inokuma et al. |
| 2004/0111012 A1 | 6/2004 | Whitman |
| 2004/0169771 A1 | 9/2004 | Washington et al. |
| 2004/0170712 A1 | 9/2004 | Sadek El Mogy |
| 2004/0249267 A1 | 12/2004 | Gilboa |
| 2005/0009982 A1 | 1/2005 | Inagaki et al. |
| 2005/0027164 A1 | 2/2005 | Barbato et al. |
| 2005/0038322 A1 | 2/2005 | Banik |
| 2005/0075538 A1 | 4/2005 | Banik et al. |
| 2005/0131279 A1 | 6/2005 | Boulais et al. |
| 2005/0148819 A1 | 7/2005 | Noguchi et al. |
| 2005/0151866 A1 | 7/2005 | Ando et al. |
| 2005/0168941 A1 | 8/2005 | Sokol et al. |
| 2005/0174428 A1 | 8/2005 | Abe |
| 2005/0206755 A1 | 9/2005 | Yokoyama et al. |
| 2005/0222499 A1 | 10/2005 | Banik et al. |
| 2005/0231591 A1 | 10/2005 | Abe |
| 2005/0234302 A1 | 10/2005 | MacKinnon et al. |
| 2005/0237412 A1 | 10/2005 | Shiohara et al. |
| 2005/0288546 A1 | 12/2005 | Sonnenschein et al. |
| 2006/0007507 A1 | 1/2006 | Inaba et al. |
| 2006/0022234 A1 | 2/2006 | Adair et al. |
| 2006/0023109 A1 | 2/2006 | Mabuchi et al. |
| 2006/0035415 A1 | 2/2006 | Wood et al. |
| 2006/0069314 A1 | 3/2006 | Farr |
| 2006/0074289 A1 | 4/2006 | Adler et al. |
| 2006/0164533 A1 | 7/2006 | Hsieh et al. |
| 2006/0181627 A1 | 8/2006 | Farrier |
| 2006/0221230 A1 | 10/2006 | Dutta et al. |
| 2006/0249765 A1 | 11/2006 | Hsieh |
| 2006/0250513 A1 | 11/2006 | Yamamoto et al. |
| 2006/0293563 A1 | 12/2006 | Banik et al. |
| 2006/0293565 A1 | 12/2006 | Uchimura et al. |
| 2007/0002134 A1 | 1/2007 | Ishihara et al. |
| 2007/0010712 A1 | 1/2007 | Negishi |
| 2007/0030262 A1 | 2/2007 | Ambo et al. |
| 2007/0030345 A1 | 2/2007 | Amling et al. |
| 2007/0046803 A1 | 3/2007 | Ahn |
| 2007/0078328 A1 | 4/2007 | Ozaki et al. |
| 2007/0091190 A1 | 4/2007 | Iwabuchi et al. |
| 2007/0094303 A1 | 4/2007 | Zwingenberger et al. |
| 2007/0129601 A1 | 6/2007 | Johnston et al. |
| 2007/0138375 A1 | 6/2007 | Lee et al. |
| 2007/0153337 A1 | 7/2007 | Kim |
| 2007/0159526 A1 | 7/2007 | Abe |
| 2007/0182842 A1 | 8/2007 | Sonnenschein et al. |
| 2007/0185549 A1 | 8/2007 | Zdeblick |
| 2007/0187703 A1 | 8/2007 | Erchak |
| 2007/0197873 A1 | 8/2007 | Birnkrant |
| 2007/0225556 A1 | 9/2007 | Ortiz et al. |
| 2007/0244364 A1 | 10/2007 | Luanava et al. |
| 2007/0244365 A1 | 10/2007 | Wiklof |
| 2007/0276187 A1 | 11/2007 | Wiklof et al. |
| 2007/0279486 A1 | 12/2007 | Bayer et al. |
| 2007/0297190 A1 | 12/2007 | Ng |
| 2008/0021271 A1 | 1/2008 | Pasero et al. |
| 2008/0042046 A1 | 2/2008 | Mabuchi |
| 2008/0045800 A2 | 2/2008 | Farr |
| 2008/0076967 A1 | 3/2008 | Couvillon, Jr. |
| 2008/0122031 A1 | 5/2008 | DeNatale et al. |
| 2008/0128740 A1 | 6/2008 | Yamashita et al. |
| 2008/0136319 A1 | 6/2008 | Yoon |
| 2008/0136945 A1 | 6/2008 | Blanquart et al. |
| 2008/0158348 A1 | 7/2008 | Karpen et al. |
| 2008/0165360 A1 | 7/2008 | Johnston |
| 2008/0185314 A1 | 8/2008 | Tomasello et al. |
| 2008/0200758 A1 | 8/2008 | Orbay et al. |
| 2008/0208006 A1 | 8/2008 | Farr |
| 2008/0211634 A1 | 9/2008 | Hopkins et al. |
| 2008/0218609 A1 | 9/2008 | Blanquart et al. |
| 2008/0218615 A1 | 9/2008 | Huang et al. |
| 2008/0239070 A1 | 10/2008 | Westwick et al. |
| 2008/0239124 A1 | 10/2008 | Mori et al. |
| 2008/0249369 A1 | 10/2008 | Seibel et al. |
| 2008/0255416 A1 | 10/2008 | Gilboa |
| 2008/0258042 A1 | 10/2008 | Krymski |
| 2008/0287798 A1 | 11/2008 | Lee et al. |
| 2008/0291290 A1 | 11/2008 | Sonoda et al. |
| 2008/0309810 A1 | 12/2008 | Smith et al. |
| 2008/0316319 A1 | 12/2008 | Nomoto |
| 2009/0012361 A1 | 1/2009 | MacKinnon et al. |
| 2009/0012368 A1 | 1/2009 | Banik |
| 2009/0015301 A1 | 1/2009 | Marchesini et al. |

(56) References Cited

U.S. PATENT DOCUMENTS

| | | |
|---|---|---|
| 2009/0021588 A1 | 1/2009 | Border et al. |
| 2009/0021628 A1 | 1/2009 | Tamakoshi |
| 2009/0040783 A1 | 2/2009 | Krupa et al. |
| 2009/0054908 A1 | 2/2009 | Zand et al. |
| 2009/0062656 A1 | 3/2009 | Hyuga |
| 2009/0074265 A1 | 3/2009 | Huang et al. |
| 2009/0076329 A1 | 3/2009 | Su et al. |
| 2009/0082630 A1 | 3/2009 | Tulley |
| 2009/0091641 A1 | 4/2009 | Hattori |
| 2009/0108176 A1 | 4/2009 | Blanquart |
| 2009/0141156 A1 | 6/2009 | Rossi et al. |
| 2009/0141180 A1 | 6/2009 | Kondo et al. |
| 2009/0154886 A1 | 6/2009 | Lewis et al. |
| 2009/0160976 A1 | 6/2009 | Chen et al. |
| 2009/0160979 A1 | 6/2009 | Xu et al. |
| 2009/0173974 A1 | 7/2009 | Shah et al. |
| 2009/0184349 A1 | 7/2009 | Dungan |
| 2009/0186780 A1 | 7/2009 | Lee et al. |
| 2009/0192390 A1 | 7/2009 | Berguer et al. |
| 2009/0200624 A1 | 8/2009 | Dai et al. |
| 2009/0200625 A1 | 8/2009 | Venezia et al. |
| 2009/0203966 A1 | 8/2009 | Mizuyoshi |
| 2009/0208143 A1 | 8/2009 | Yoon et al. |
| 2009/0212397 A1 | 8/2009 | Tuttle |
| 2009/0216080 A1 | 8/2009 | Nakamura |
| 2009/0225548 A1 | 9/2009 | Narita |
| 2009/0227847 A1 | 9/2009 | Tepper et al. |
| 2009/0230287 A1 | 9/2009 | Anderson et al. |
| 2009/0236500 A1 | 9/2009 | Shah et al. |
| 2009/0256905 A1 | 10/2009 | Tashiro |
| 2009/0265490 A1 | 10/2009 | Setya et al. |
| 2009/0268147 A1 | 10/2009 | Tang et al. |
| 2009/0278963 A1 | 11/2009 | Shah et al. |
| 2009/0292168 A1 | 11/2009 | Farr |
| 2009/0306478 A1 | 12/2009 | Mizuyoshi |
| 2009/0316116 A1 | 12/2009 | Melville et al. |
| 2009/0322911 A1 | 12/2009 | Blanquart |
| 2009/0322912 A1 | 12/2009 | Blanquart |
| 2010/0026824 A1 | 2/2010 | Chen |
| 2010/0039156 A1* | 2/2010 | Yamaguchi ......... G09G 3/2096 327/291 |
| 2010/0049180 A1 | 2/2010 | Wells et al. |
| 2010/0059802 A1 | 3/2010 | Chen |
| 2010/0118932 A1 | 5/2010 | Luo et al. |
| 2010/0121142 A1 | 5/2010 | OuYang et al. |
| 2010/0134662 A1 | 6/2010 | Bub |
| 2010/0137684 A1 | 6/2010 | Shibasaki et al. |
| 2010/0140732 A1 | 6/2010 | Eminoglu et al. |
| 2010/0157037 A1 | 6/2010 | Iketani et al. |
| 2010/0157039 A1 | 6/2010 | Sugai |
| 2010/0157117 A1 | 6/2010 | Wang |
| 2010/0171429 A1 | 7/2010 | Garcia et al. |
| 2010/0178722 A1 | 7/2010 | de Graff et al. |
| 2010/0182446 A1 | 7/2010 | Matsubayashi |
| 2010/0194860 A1 | 8/2010 | Mentz et al. |
| 2010/0198009 A1 | 8/2010 | Farr et al. |
| 2010/0204546 A1 | 8/2010 | Hassidov et al. |
| 2010/0228089 A1 | 9/2010 | Hoffman et al. |
| 2010/0245647 A1 | 9/2010 | Honda et al. |
| 2010/0276572 A1 | 11/2010 | Iwabuchi et al. |
| 2010/0290100 A1 | 11/2010 | Karasawa |
| 2010/0295978 A1 | 11/2010 | Nakamura et al. |
| 2010/0305406 A1 | 12/2010 | Braun et al. |
| 2010/0315333 A1 | 12/2010 | Hsu |
| 2011/0034769 A1 | 2/2011 | Adair et al. |
| 2011/0034770 A1 | 2/2011 | Endo et al. |
| 2011/0037876 A1 | 2/2011 | Talbert et al. |
| 2011/0049591 A1* | 3/2011 | Nakatani ......... H01L 27/14647 257/292 |
| 2011/0050874 A1* | 3/2011 | Reshef ................ H04N 5/378 348/65 |
| 2011/0050969 A1 | 3/2011 | Nishihara |
| 2011/0055447 A1 | 3/2011 | Costa |
| 2011/0063428 A1 | 3/2011 | Sonnenschein et al. |
| 2011/0115663 A1 | 5/2011 | Bogaerts |
| 2011/0121654 A1 | 5/2011 | Recker et al. |
| 2011/0128408 A1 | 6/2011 | Ishigaki et al. |
| 2011/0181709 A1 | 7/2011 | Wright et al. |
| 2011/0181840 A1 | 7/2011 | Cobb |
| 2011/0184239 A1 | 7/2011 | Wright et al. |
| 2011/0184243 A1 | 7/2011 | Wright et al. |
| 2011/0208004 A1 | 8/2011 | Feingold et al. |
| 2011/0228790 A1 | 9/2011 | Martin de Nicolas |
| 2011/0237882 A1 | 9/2011 | Saito |
| 2011/0237884 A1 | 9/2011 | Saito |
| 2011/0238977 A1 | 9/2011 | Talbert et al. |
| 2011/0242300 A1 | 10/2011 | Hashimoto |
| 2011/0245605 A1 | 10/2011 | Jacobsen et al. |
| 2011/0263941 A1 | 10/2011 | Wright et al. |
| 2011/0279679 A1 | 11/2011 | Samuel et al. |
| 2011/0288374 A1 | 11/2011 | Hadani et al. |
| 2011/0292258 A1 | 12/2011 | Adler et al. |
| 2011/0295061 A1 | 12/2011 | Haramaty et al. |
| 2011/0298908 A1 | 12/2011 | Murakami |
| 2012/0004508 A1 | 1/2012 | McDowall et al. |
| 2012/0014563 A1 | 1/2012 | Bendall |
| 2012/0029279 A1 | 2/2012 | Kucklick |
| 2012/0035419 A1 | 2/2012 | Ashida et al. |
| 2012/0035434 A1 | 2/2012 | Ferren et al. |
| 2012/0041267 A1 | 2/2012 | Benning et al. |
| 2012/0041534 A1 | 2/2012 | Clerc et al. |
| 2012/0050592 A1 | 3/2012 | Oguma |
| 2012/0071720 A1 | 3/2012 | Banik et al. |
| 2012/0078052 A1 | 3/2012 | Cheng |
| 2012/0113506 A1 | 5/2012 | Gmitro et al. |
| 2012/0120282 A1 | 5/2012 | Goris |
| 2012/0140302 A1 | 6/2012 | Xie et al. |
| 2012/0147229 A1 | 6/2012 | Shah et al. |
| 2012/0265196 A1 | 10/2012 | Turner et al. |
| 2012/0293699 A1 | 11/2012 | Blanquart et al. |
| 2012/0307030 A1* | 12/2012 | Blanquart ......... H01L 27/14641 348/76 |
| 2013/0010166 A1 | 1/2013 | Morisaki et al. |
| 2013/0126707 A1 | 5/2013 | Blanquart |
| 2013/0126708 A1 | 5/2013 | Blanquart |
| 2013/0126709 A1 | 5/2013 | Blanquart |
| 2013/0144122 A1 | 6/2013 | Adair et al. |
| 2013/0158346 A1 | 6/2013 | Soper et al. |
| 2013/0176409 A1* | 7/2013 | Kotani ............... A61B 1/00009 348/65 |
| 2013/0222165 A1 | 8/2013 | David et al. |
| 2013/0242069 A1 | 9/2013 | Kobayashi |
| 2013/0264465 A1* | 10/2013 | Dai ................... H01L 27/14601 250/208.1 |
| 2013/0292854 A1 | 11/2013 | Lua et al. |
| 2013/0300837 A1 | 11/2013 | DiCarlo et al. |
| 2014/0052004 A1 | 2/2014 | D'Alfonso et al. |
| 2014/0073852 A1 | 3/2014 | Banik et al. |
| 2014/0104466 A1 | 4/2014 | Fossum |
| 2014/0160259 A1 | 6/2014 | Blanquart et al. |
| 2014/0175591 A1 | 6/2014 | Tian et al. |
| 2014/0176691 A1* | 6/2014 | Minakuchi ............ H04N 7/183 348/65 |
| 2014/0198240 A1 | 7/2014 | Rhoads |
| 2014/0203084 A1 | 7/2014 | Wang |
| 2014/0217268 A1 | 8/2014 | Schleipen et al. |
| 2014/0267851 A1 | 9/2014 | Rhoads |
| 2014/0275783 A1 | 9/2014 | Blanquart |
| 2014/0285645 A1 | 9/2014 | Blanquart et al. |
| 2014/0300698 A1 | 10/2014 | Wany |
| 2014/0354788 A1 | 12/2014 | Yano |
| 2014/0364689 A1 | 12/2014 | Adair et al. |
| 2015/0215560 A1 | 7/2015 | Blanquart et al. |
| 2016/0155765 A1 | 6/2016 | Blanquart |
| 2016/0190197 A1 | 6/2016 | Blanquart |
| 2016/0256041 A1 | 9/2016 | Blanquart et al. |
| 2017/0221945 A1 | 8/2017 | Blanquart |
| 2019/0007588 A1 | 1/2019 | Blanquart et al. |
| 2019/0008375 A1 | 1/2019 | Blanquart et al. |
| 2019/0068909 A1 | 2/2019 | Kaibara |
| 2019/0269304 A1 | 9/2019 | Blanquart |
| 2020/0129054 A1 | 4/2020 | Blanquart |
| 2020/0138279 A1 | 5/2020 | Blanquart et al. |

(56) References Cited

U.S. PATENT DOCUMENTS

FOREIGN PATENT DOCUMENTS

| | | |
|---|---|---|
| CN | 1398407 A | 2/2003 |
| CN | 1953193 A | 4/2007 |
| CN | 1992821 A | 7/2007 |
| CN | 100407433 C | 7/2008 |
| CN | 101314154 | 7/2008 |
| CN | 101281918 A | 10/2008 |
| CN | 100502024 C | 6/2009 |
| CN | 101640211 A | 2/2010 |
| CN | 101013714 B | 5/2010 |
| CN | 101715644 A | 5/2010 |
| CN | 101848344 | 9/2010 |
| CN | 101939841 A | 1/2011 |
| CN | 101978598 A | 2/2011 |
| CN | 102006427 A | 4/2011 |
| CN | 102266217 A | 12/2011 |
| CN | 102397049 A | 4/2012 |
| CN | 102450998 A | 5/2012 |
| CN | 103094653 A | 5/2013 |
| CN | 103636000 A | 3/2014 |
| CN | 103650476 A | 3/2014 |
| CN | 2012800337461 B | 10/2016 |
| EP | 1618833 A1 | 1/2006 |
| EP | 1628348 A1 | 2/2006 |
| EP | 2108305 A1 | 10/2009 |
| EP | 2234387 A1 | 9/2010 |
| EP | 2302905 A1 | 3/2011 |
| EP | 2442558 A1 | 4/2012 |
| EP | 1845835 B1 | 11/2014 |
| IL | 229396 | 7/2016 |
| IL | 229397 | 7/2016 |
| JP | H05-268534 | 5/1995 |
| JP | H09-140664 | 12/1998 |
| JP | 2001339057 | 7/2001 |
| JP | 2002329851 | 11/2002 |
| JP | 2004241490 | 8/2004 |
| JP | 2004348676 | 12/2004 |
| JP | 2006025852 | 2/2006 |
| JP | 2006049361 | 2/2006 |
| JP | 2007214191 | 8/2007 |
| JP | 2007214772 | 8/2007 |
| JP | 2007228460 | 9/2007 |
| JP | 200848313 | 2/2008 |
| JP | 2008235478 | 10/2008 |
| JP | 07-136109 A | 12/2008 |
| JP | 2008290817 A | 12/2008 |
| JP | 2009100380 | 5/2009 |
| JP | 2009206958 A | 9/2009 |
| JP | 2010252396 | 11/2010 |
| JP | 2010273757 | 12/2010 |
| JP | 2011050969 | 3/2011 |
| JP | 2011114733 | 6/2011 |
| JP | 2014514891 A | 6/2014 |
| JP | 2014515955 A | 7/2014 |
| JP | 2016520341 A | 7/2016 |
| KR | 1020100106920 | 10/2010 |
| KR | 1020100126749 | 12/2010 |
| WO | 9413191 | 6/1994 |
| WO | 1996005693 A1 | 2/1996 |
| WO | 200108549 A1 | 2/2001 |
| WO | 2004093438 | 10/2004 |
| WO | 2006080015 A2 | 8/2006 |
| WO | 2006129762 A1 | 12/2006 |
| WO | 2009120228 A1 | 10/2009 |
| WO | 2009135255 | 11/2009 |
| WO | 2012155142 A1 | 11/2012 |
| WO | 2012155143 A1 | 11/2012 |
| WO | 2012155150 A1 | 11/2012 |
| WO | 2012155152 A1 | 11/2012 |
| WO | 2014018948 A2 | 1/2014 |
| WO | 2014145246 A1 | 9/2014 |
| WO | 2014145248 A1 | 9/2014 |

* cited by examiner

| | | |
|---|---|---|
| R_CLK | I | Recovered Clock. This is the input from the clock and data recovery (CDR) |
| REF_CLK | I | Reference Clock. This is the input from the known reference clock |
| CTL | I | Control inputs from the supervisory software. This sets the big and little push thresholds as well as the target frequency |
| PUSH | O | 0: don't push the frequency, 1: push the frequency |
| UP_DOWN | O | 0: if PUSH then push down, 1: if PUSH then push up |
| BIG_LITTLE | O | 0: if PUSH then push a little, 1: if PUSH then push big |

FIG. 12

IMAGE SENSOR SYNCHRONIZATION WITHOUT INPUT CLOCK AND DATA TRANSMISSION CLOCK

CROSS-REFERENCE TO RELATED APPLICATIONS

This application is a continuation of U.S. patent application Ser. No. 14/214,790, filed Mar. 15, 2014 and which claims the benefit of U.S. Provisional Application No. 61/800,502, filed Mar. 15, 2013, and U.S. Provisional Application No. 61/790,590, filed Mar. 15, 2013, both of which are hereby incorporated by reference herein in their entireties, including but not limited to those portions that specifically appear hereinafter, the incorporation by reference being made with the following exception: In the event that any portion of any of the above-referenced provisional applications is inconsistent with this application, this application supersedes said above-referenced provisional applications.

STATEMENT REGARDING FEDERALLY SPONSORED RESEARCH OR DEVELOPMENT

Not Applicable.

BACKGROUND

Advances in technology have provided improvements in imaging capabilities for medical use. One area that has enjoyed some of the most beneficial advances is that of endoscopic surgical procedures because of the advances in the components that make up an endoscope.

The disclosure relates generally to electromagnetic sensing and sensors and more particularly related to data transfer. The features and advantages of the disclosure will be set forth in the description which follows, and in part will be apparent from the description, or may be learned by the practice of the disclosure without undue experimentation. The features and advantages of the disclosure may be realized and obtained by means of the instruments and combinations particularly pointed out in the disclosure.

BRIEF DESCRIPTION OF THE DRAWINGS

Non-limiting and non-exhaustive implementations of the disclosure are described with reference to the following figures, wherein like reference numerals refer to like parts throughout the various views unless otherwise specified. Advantages of the disclosure will become better understood with regard to the following description and accompanying drawings where:

FIG. 12 illustrates a table of operational parameters in accordance with the principles and teachings of the disclosure;

DETAILED DESCRIPTION

Figure 1:
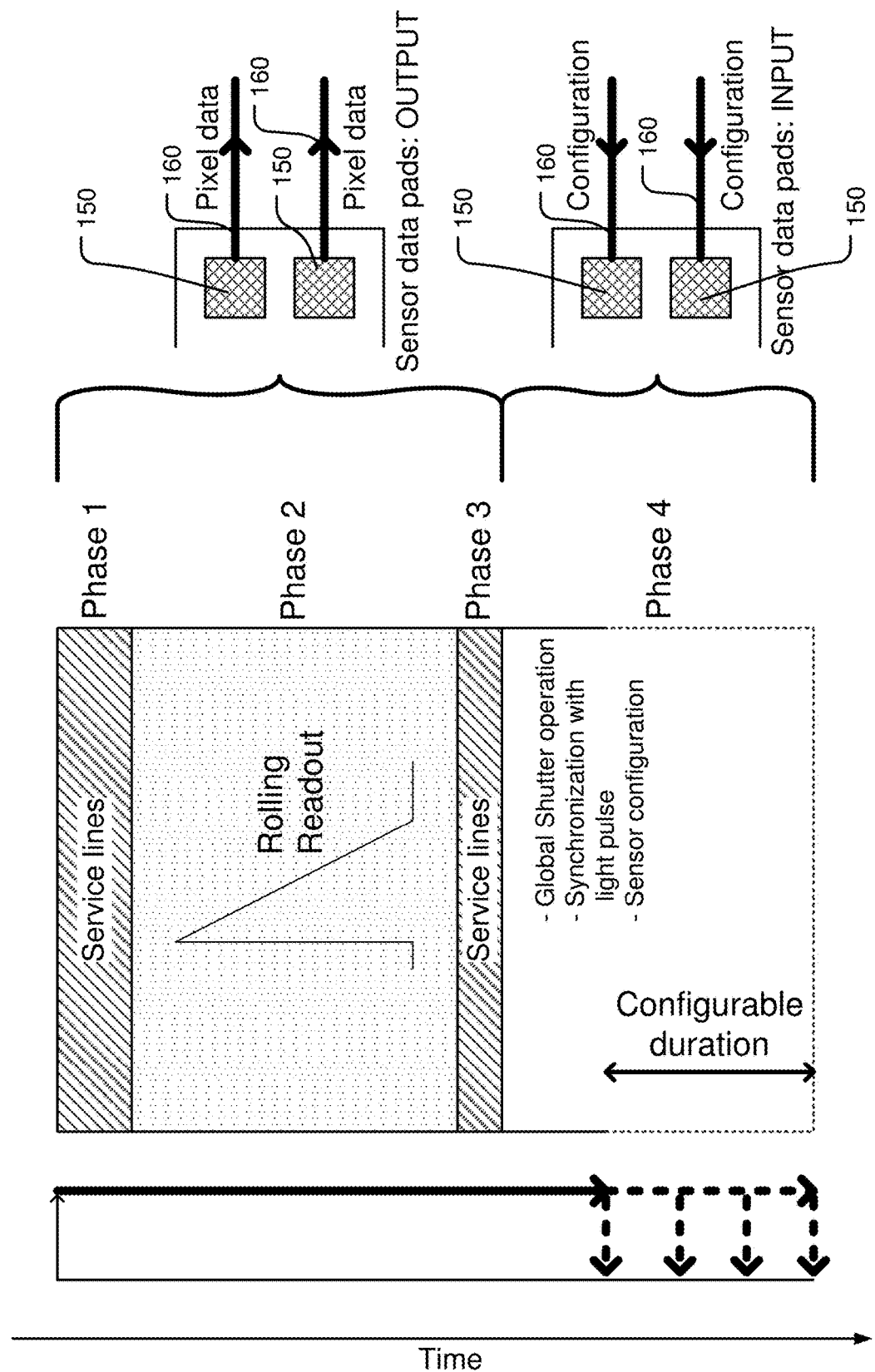
FIG. 1 illustrates a schematic representation of an embodiment of the operation of a pixel array and image sensor in accordance with the principles and teachings of the disclosure.

The disclosure extends to methods, systems, and computer based products for digital imaging that may be primarily suited to medical applications. In the following description of the disclosure, reference may be made to the accompanying drawings, which form a part hereof, and in which is shown by way of illustration specific implementations in which the disclosure may be practiced. It may be understood that other implementations may be utilized and structural changes may be made without departing from the scope of the disclosure.

The disclosure extends to systems and methods for reducing imaging sensor pad count by negating the need for an output clock (clock-less data transmission) and the need for an input clock. The basic strategy is that the sensor issues a continuous stream of 1s and 0s on its data port(s) upon power-up, in order for the data receiver within the support electronics of the camera to synchronize to it using a CDR (Clock Data Recovery) circuit (clock training). If needed, the continuous stream can be enabled during normal operation by toggling one configuration register bit. Once the receiver has locked onto this training pattern, normal sensor imaging operation may proceed. In order to maintain the lock, long periods without transitions may be avoided by including a single invert bit for the digital value issued for each pixel.

Traditional rod-lens endoscopes, used for laparoscopy, arthroscopy, urology, gynecology and ENT (ear-nose-throat) procedures are expensive to manufacture owing to their complex optical composition. The incident image information is transported in the optical domain all the way along its length. Typically it is optically coupled to hand-piece unit wherein the image sensing device(s) reside. This type of rigid endoscope is also delicate and prone to damage during handling, use and sterilization. The necessary repair and sterilization processes add further expense to each procedure for which they are utilized.

Advances in image sensing technology have led to CMOS devices that are cheap to manufacture and are highly customizable. Much of the external circuitry that was necessary to operate CCD-based sensors may be integrated into the same chip as the pixel array and lower operation voltages are needed. Therefore CMOS-based cameras are much cheaper and easier to manufacture and may be much more versatile than their CCD-based counterparts. For similar reasons, CMOS sensors are appearing more and more within endoscope systems.

Less expensive endoscopes to manufacture may be realized by placing the image sensing device at the distal end of the endoscope, since the optical transport assembly may be effectively replaced by a simple plastic lens stack. They may be so inexpensive that it may make more financial sense to have them be manufactured for single use only, to be subsequently disposed of or recycled, since that negates the repair and sterilization processes.

The difficulty in creating such an endoscope solution is in maintaining image quality, since the region into which the sensor must fit is highly space constrained in both dimensions. Reducing the sensor area generally implies a reduction in pixel count and/or pixel area, which may impact the resolution, sensitivity and dynamic range. Normally, endoscope systems are geared toward sensing steady broadband illumination and providing color information by virtue of arrays that are segmented into pixels of three or more ranges of wavelength sensitivity. This is done by crafting an individual color filter over each pixel, the Bayer mosaic being the most common solution.

One way to avoid resolution loss is to eliminate the color filters since with the Bayer mosaic, e.g., there may be up to a factor $1/\sqrt{2}$ loss in luminance resolution (in x or y) as compared with the native array resolution. The color information in such a case can be provided by pulsing a laser or LED-based illuminants with different wavelengths or combinations thereof during separate frame captures. Applicant has developed approaches and solutions to this, which allow for high definition quality at progressive frame rates of 60 Hz or higher, by virtue of a special sensor design. Further developments by Applicant have allowed for the peripheral circuitry to be reduced to its minimal area while transmitting image data off chip in the digital domain.

A significant consumer of chip area is each bond pad, used to provide power or input/output signals to and from the sensor chip. Therefore, in striving for minimal area it is desirable to reduce the number of bond pads as much as possible.

Synchronization of the sensor data may be performed without an output clock. High speed data transmission may normally be accompanied by a clock for synchronization purposes. This has the inconvenience of one additional pad for CMOS or 2 additional pads if the LVDS standard is in use. An alternative system and method of latching high speed data may be to embed the clock signal within the data stream itself (clock encoding). At the receiving end, the data stream may be decoded in order to extract the clock, which is then used to latch the data. The penalty or disadvantage of this system and method may be that a significant burden is added to the payload and the output frequency has to be significantly increased.

In this disclosure a method is described, which may prevent the need for output clock pads without the use of clock encoding. Instead, the disclosure may use the CDR (Clock Data Recovery) system on the camera unit to correctly latch the incoming data. In the CDR system, an internal PLL (Phase Locked Loop) is used to lock on the incoming data frequency and to latch the data. The locking process requires data transitions in order for its PLL to converge. Typically, a minimum number of transitions for initial locking (and re-locking) will be specified along with a maximum number of consecutive allowed bits without transition, (which may be required in order for the PLL to stay locked).

Referring now to the figures, FIG. 1 illustrates the internal timing of an embodiment of a minimal area custom CMOS image sensor. Each frame period may comprise 4 distinct phases. During phases 1 and 3, data may be issued from the sensor through sensor data pads 150, which are not signal samples from physical pixels. Rather they are data concerned with the synchronization of the chip to the camera system and for data locking. Phase 2 is concerned with the sensor rolling readout (internal timing, synchronization and readout of physical pixels) while phase 4 is for the purpose of sensor configuration. During the configuration phase, the sensor output data lines 160 may be reversed to accept incoming configuration commands. There is a risk that during phase 4, the CDR circuit in the camera unit will become unlocked, since the sensor will not send any data transitions during a defined period of time. The service lines of phase 1 may be used to send a continuous stream of data transitions, however, to re-lock the camera unit CDR circuit, should they be required.

Figure 2:
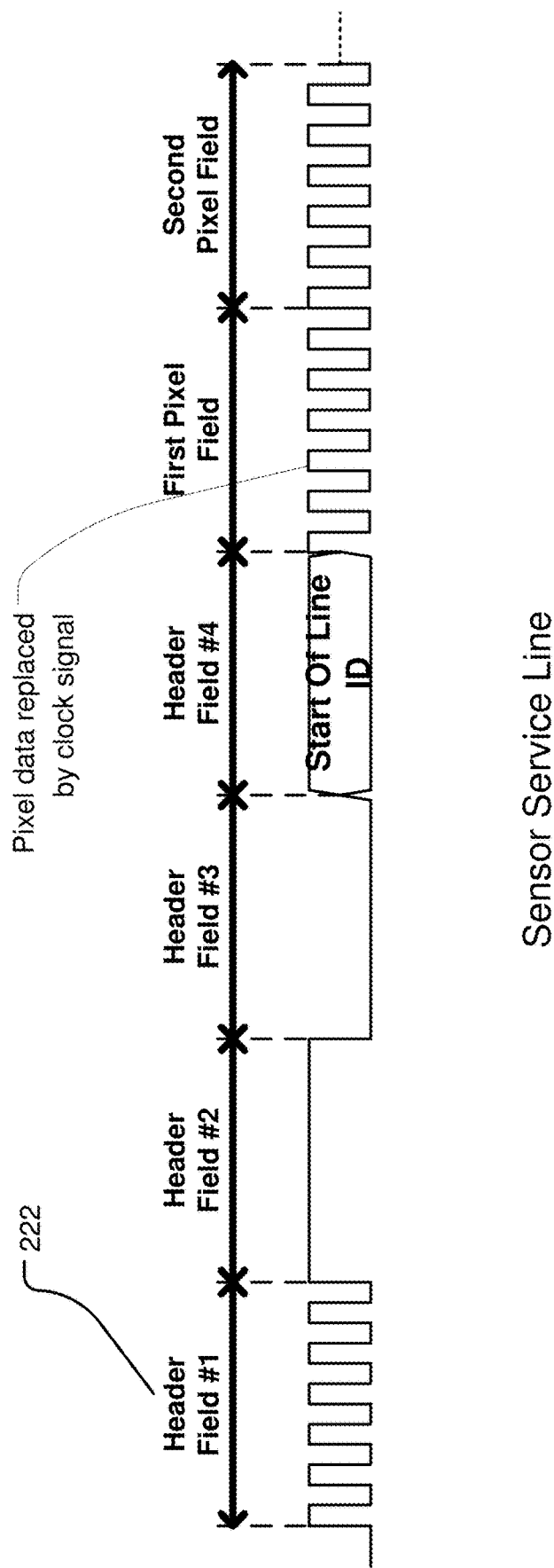
FIG. 2 illustrates graphical representation of data transfer with in a sensor service line in accordance with the principles and teachings of the disclosure.

FIG. 2 illustrates an example of such a stream where a clock-like signal is inserted into the output data stream, where normally there would be pixel data (clock recovery lines) 210. It should be noted that other clock patterns may be used and fall within the scope of this disclosure. As seen best in FIG. 2, a line header 222 may be defined, in order for the camera system to differentiate between clock recovery lines and pixel data lines. The number of clock recovery lines in phase 1 is adjustable via a register setting.

Figure 3:
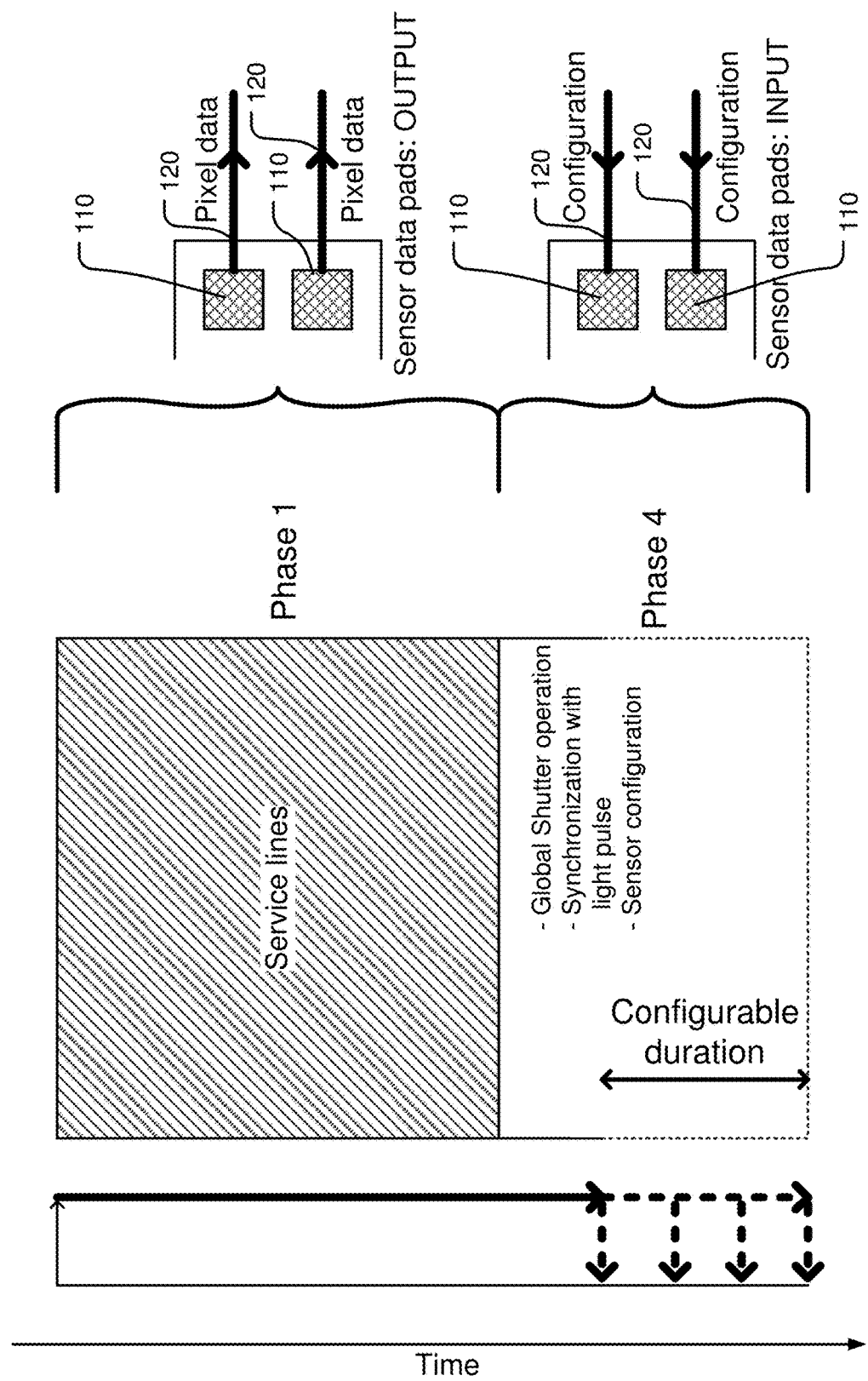
FIG. 3 illustrates a schematic representation of an embodiment of the operation of a pixel array and image sensor in accordance with the principles and teachings of the disclosure.

It should be noted that the duration of phase 4 may be below about ~5 ms -10 ms, which allows for a very limited number of clock recovery lines. Therefore, the number of transitions available to re-lock the system may be correspondingly low. This should not normally be an issue, however, because the PLL voltage of the camera unit CDR does not have time to drift very far away from the locking voltage during phase 4. In the event of the PLL voltage being significantly far from the locking voltage (at start-up for example), the receiver needs a significantly greater number of transitions. For that purpose, the sensor can be programmed to be in a full clock training sequence wherein phases 1, 2 and 3 may be merged to become continuous period of clock training. See, for example, FIG. 3. Once the camera unit CDR has locked, the sensor may resume normal operation with phase 1 providing the smaller adjustments needed for re-locking of the camera unit CDR. Therefore, the CDR specification regarding the minimal number of transitions to lock or re-lock is taken care of by the 2 operation modes described.

In order to address the CDR specification concerned with the maximal number of bits between transitions (to ensure that the CDR does not lose its lock), a method which is based upon a special encoding of the pixel data, may be used.

Figure 4:
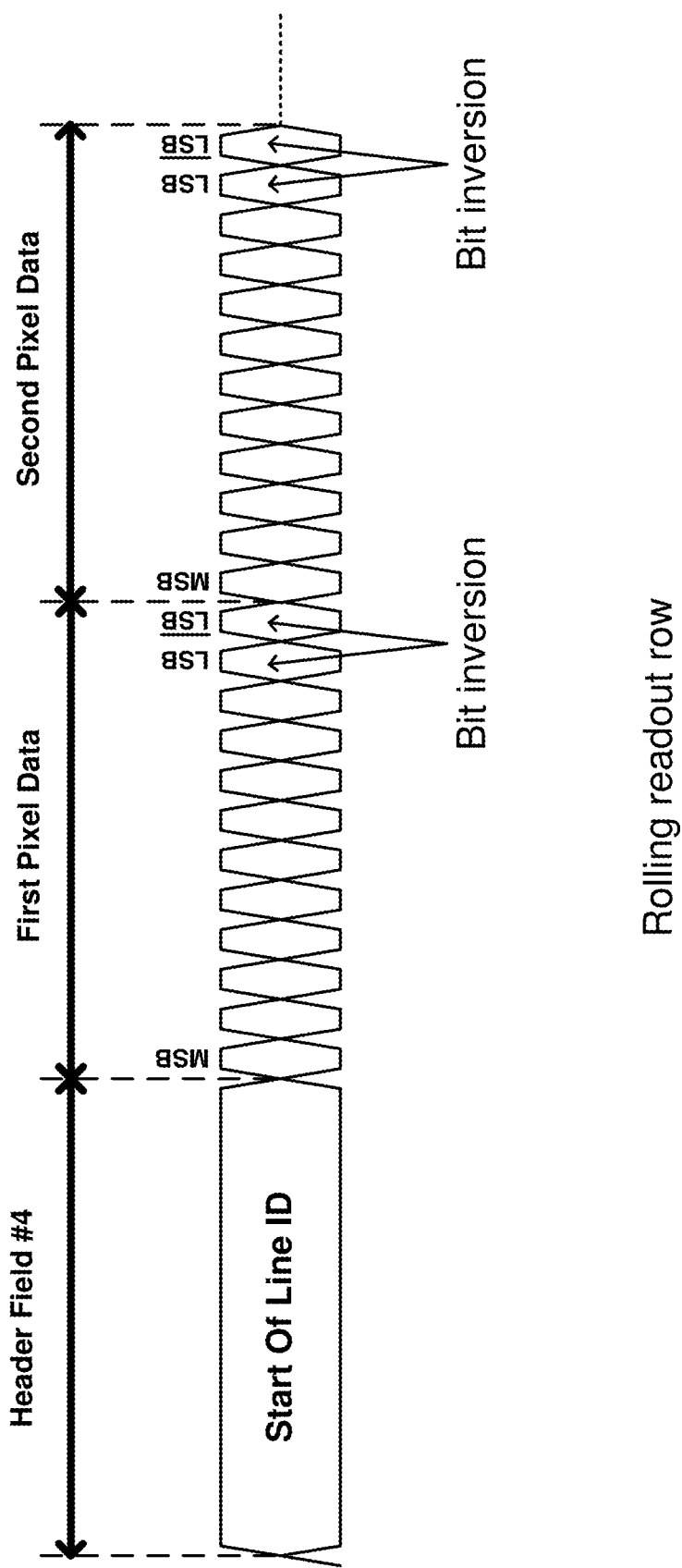
FIG. 4 illustrates graphical representation of a rolling readout output data of a sensor in accordance with the principles and teachings of the disclosure.

In FIG. 4, an example of such a special pixel encoding is shown in which the actual pixel data values are 11 bits, (with the MSB transmitted first and the LSB, last). A 12th bit may be added to each pixel's data, which is always an inverted version of the 11th (least significant) true bit. This results in an encoding with very little overhead. A high transition rate may be obtained during the transmission of pixel data, thereby avoiding any possibility of the camera unit CDR becoming unlocked.

Figure 5B:
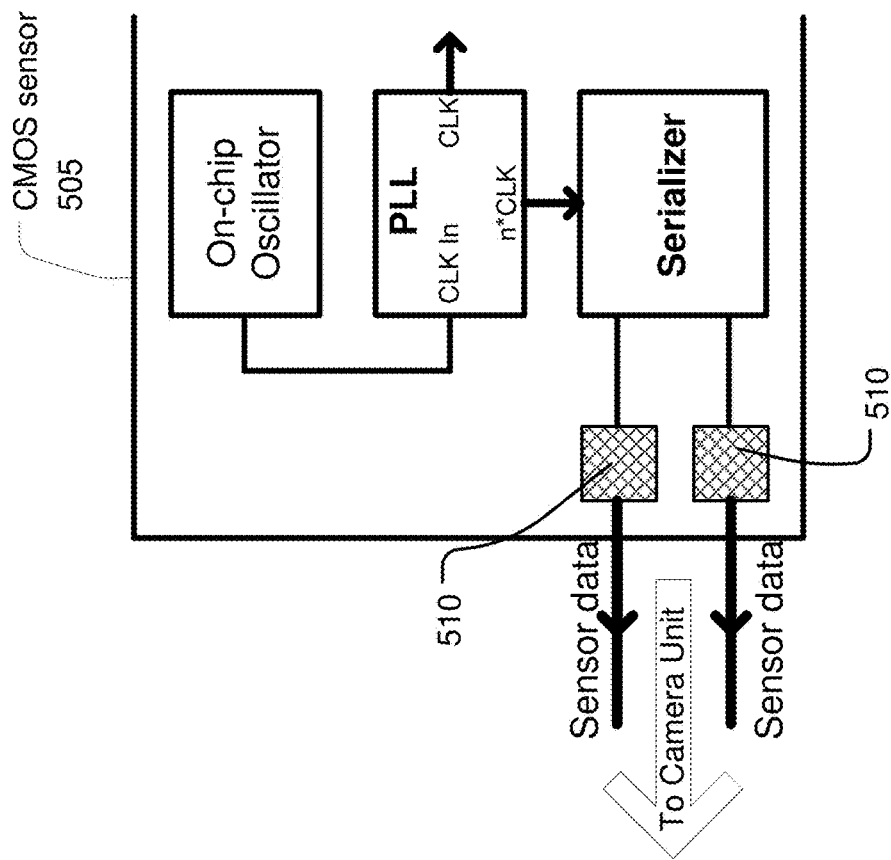
FIG. 5B illustrates a schematic representation of an embodiment of an image sensor having an on-chip oscillator in accordance with the principles and teaching of the disclosure.
Figure 5A:
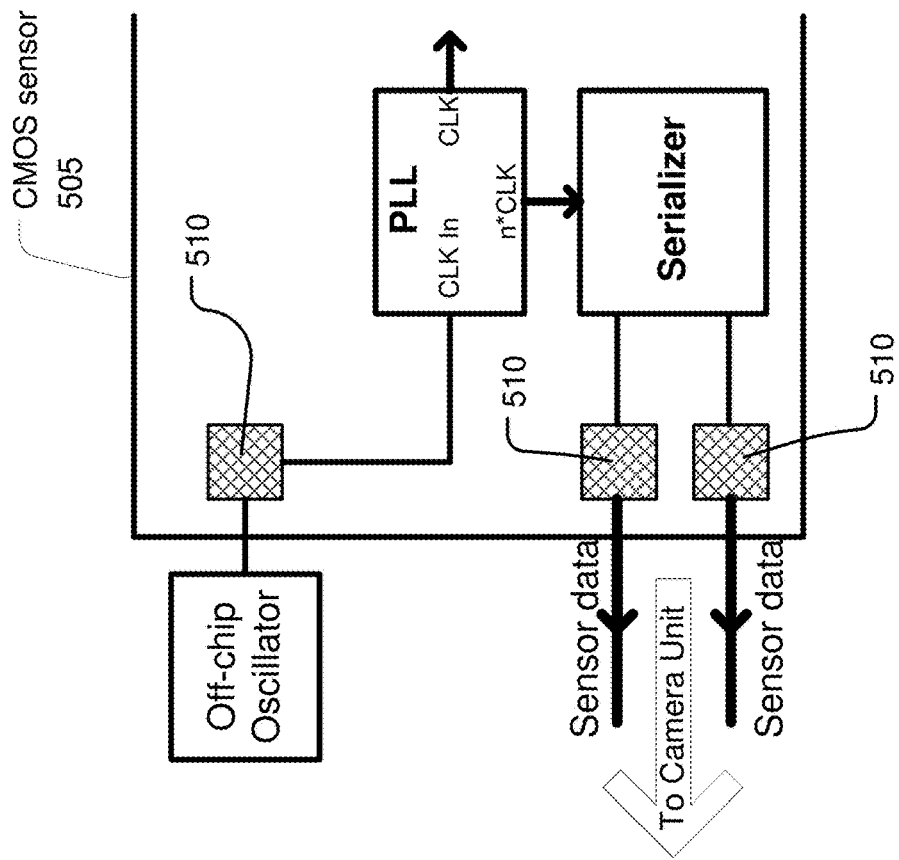
FIG. 5A illustrates a schematic representation of an embodiment of an image sensor having an off-chip oscillator in accordance with the principles and teaching of the disclosure.

FIGS. 5A and 5B illustrate two conventional methods to generate a clock signal for an image sensor 505. FIG. 5A relates to an off-chip device that may be a crystal oscillator and a Phase Lock Loop (PLL) circuit. Although very precise, this method adds the burden of one pad 510 and one active component. Moreover the active component may require low speed control programming that further increases the conductor count. This may be a disadvantage at the distal tip of an endoscope where space is very limited. FIG. 5B represents a clock generation using on-chip circuitry. This method provides an advantageous result in terms of pad 510 and conductor counts. However, such circuits may be inconsistent and exhibit significant variability from chip to chip. Moreover, they are often temperature dependent and can be sensitive to any change in temperature. These drawbacks prevent use in applications like video where the frame rate needs to be ultra-precise.

This disclosure describes a method and system of generating an on-chip precise clock without adding any external components. It should be further noted that by virtue of re-purposing the sensor data output pads and low speed control programming pads (which may be the same bidirectional pads as described above), no extra pad nor conductor is required.

Figure 6:
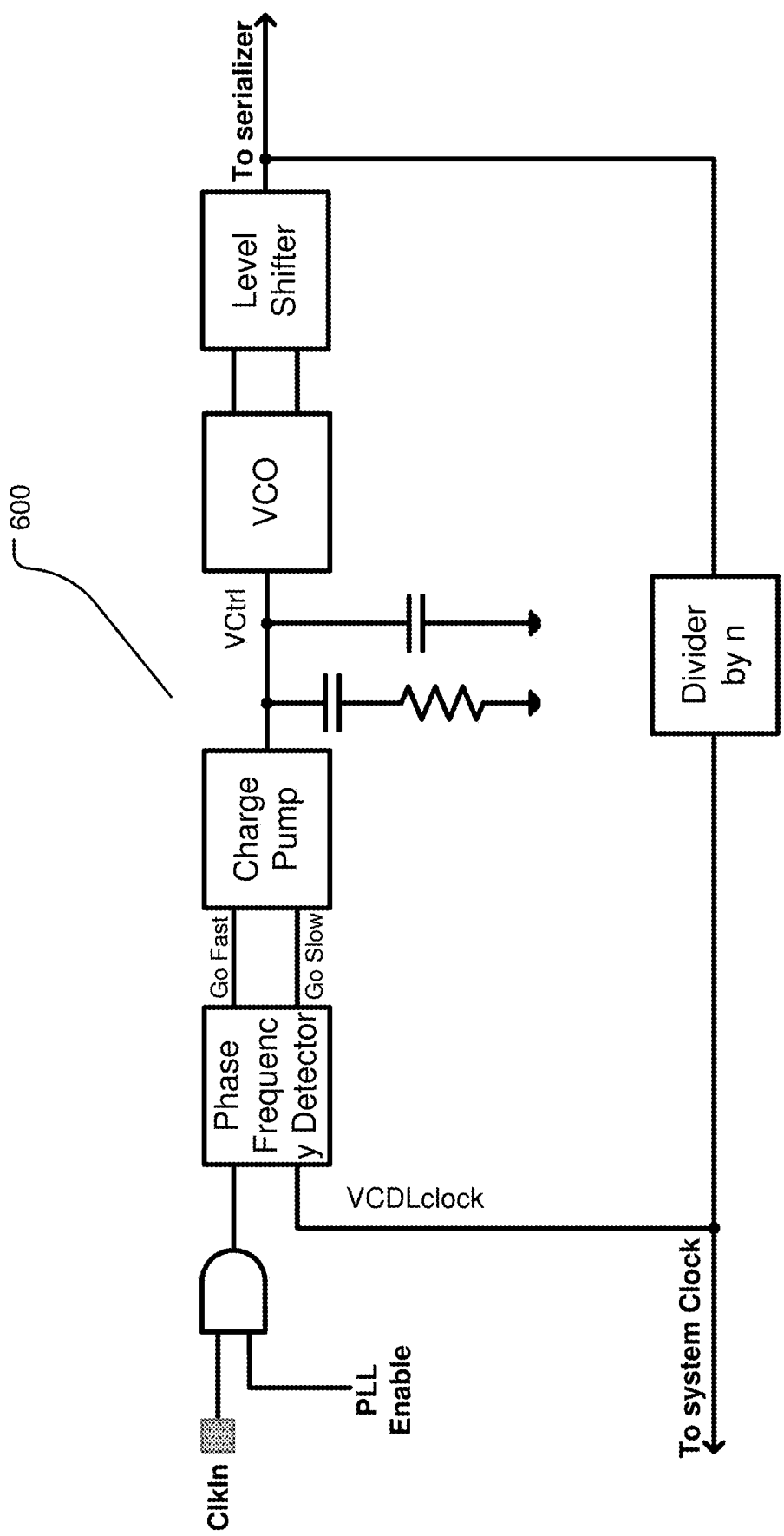
FIG. 6 illustrates a schematic representation of an embodiment of circuitry for clock management and data sequencing in accordance with the principles and teaching of the disclosure.

FIG. 6 depicts a conventional PLL 600. The VCDL (voltage controlled delay line) clock is compared to the incoming clock with the frequency detector and up-pushes or down-pushes are issued to the external VCO (voltage controlled oscillator) depending on the frequency detector comparison result. This system may dynamically react and adjust to ensure that the VCDL clock always matches the input clock.

The concept behind the system and method is to create a PLL that overlaps between the sensor and the camera unit, taking advantage of the communication protocol that already exists between the two devices. In an embodiment, the system and method may move the frequency detector from the sensor PLL to the camera unit. Its input can then be attached to the precise clock provided by camera unit oscillator. This local oscillator has the additional benefit of not increasing the sensor pad count because located in the camera unit. In the embodiment, a digital feed-forward and feedback nodes in the PLL may be selected and matched to the feed-forward system node (low speed control programming from camera unit to sensor) and feedback system node (pixel data output from sensor to camera unit).

Figure 7:
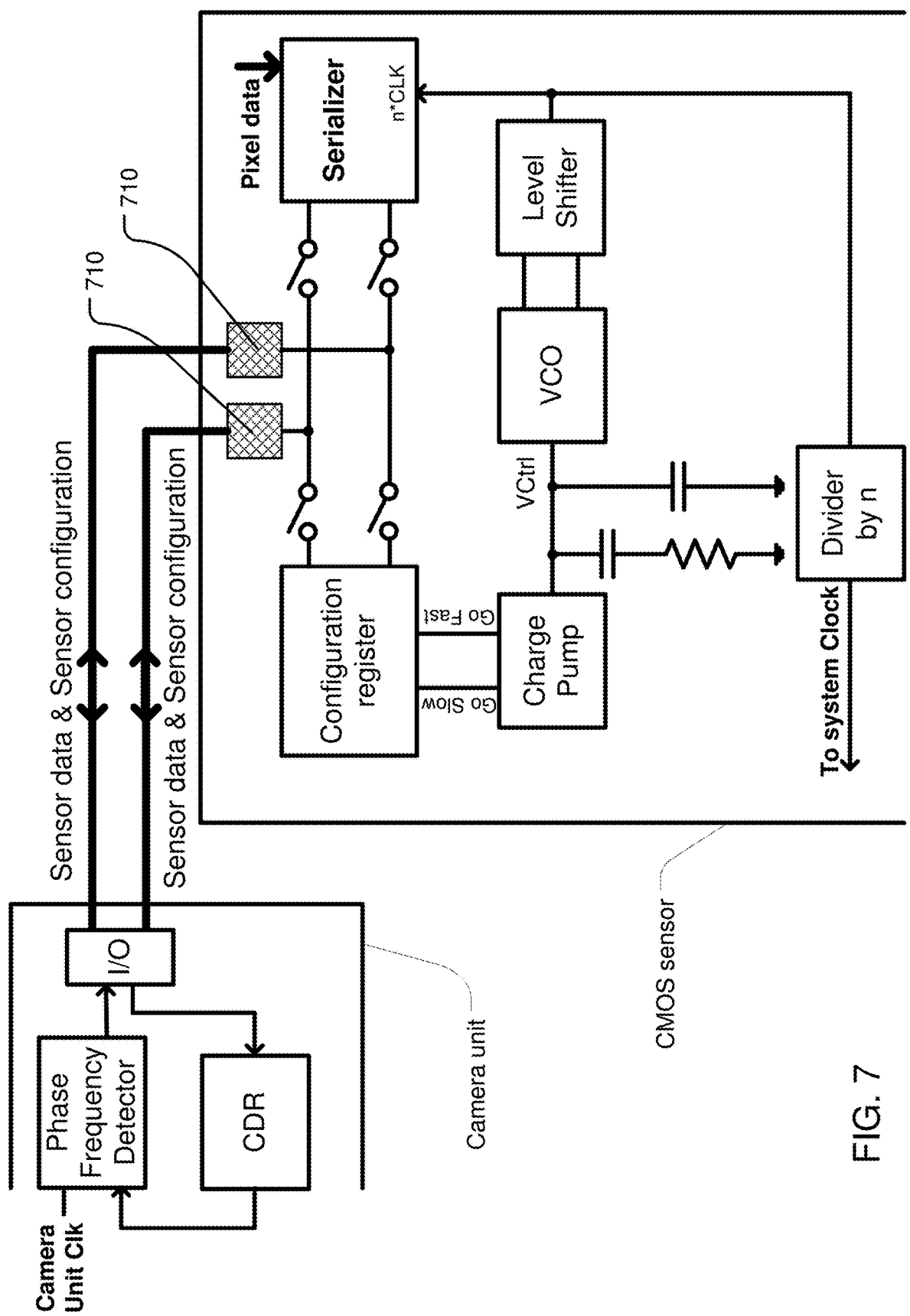
FIG. 7 illustrates a schematic representation of an embodiment of circuitry for clock management and data sequencing between a camera unit and a CMOS sensor in accordance with the principles and teaching of the disclosure.

In the embodiment of FIG. 7, the feed-forward node may be chosen to be the go-fast go-slow signals and will be updated using the sensor low speed control programming. The feedback node may be chosen to be the multiplied clock prior to the divider by n. This multiplied frequency may be used to serialize the pixel data and is decoded by the CDR in the camera unit, which can then be fed back to the frequency detector. Such an embodiment does not increase the pad 710 count or the conductor count.

Figure 8:
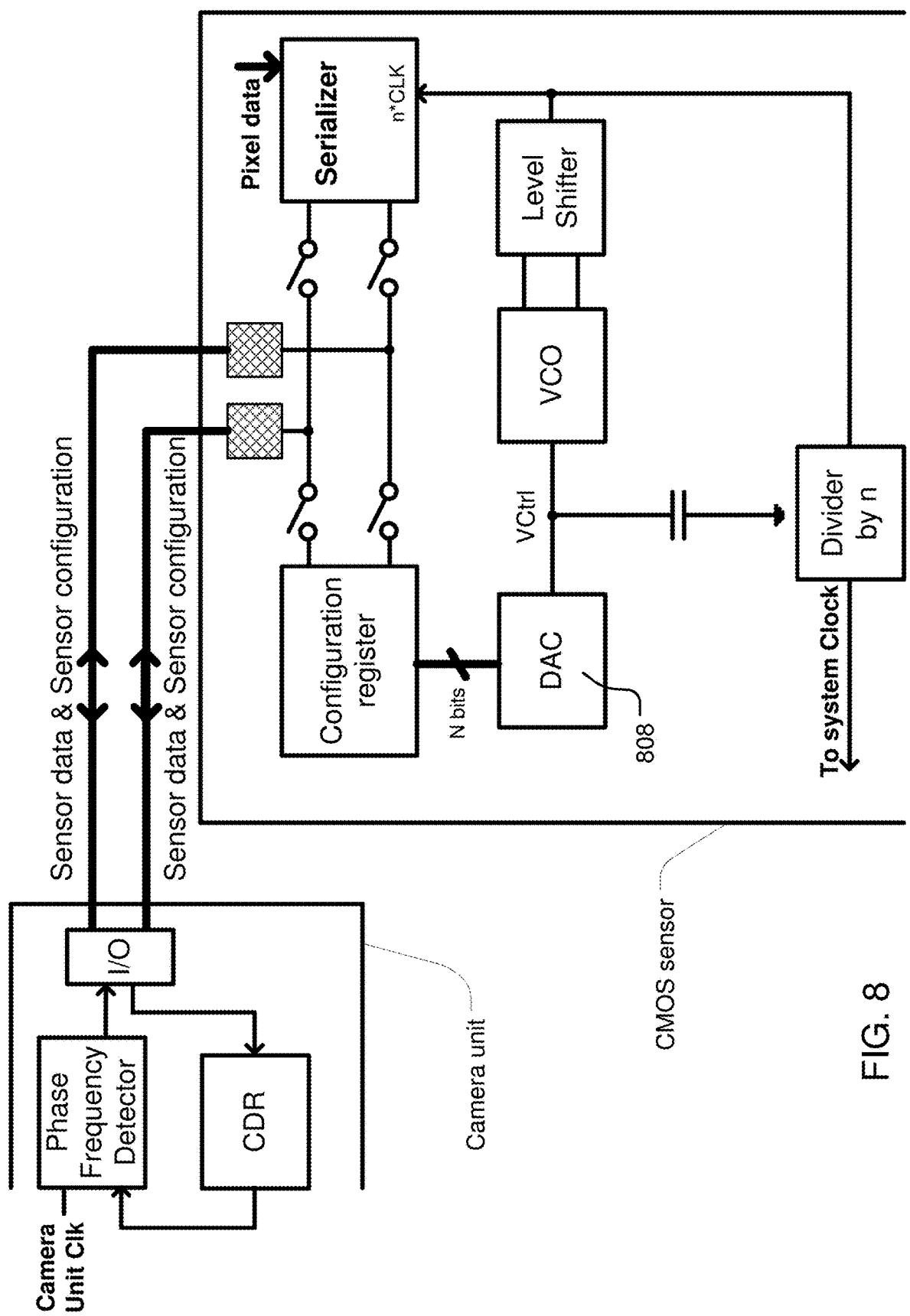
FIG. 8 illustrates a schematic representation of an embodiment of circuitry for clock management and data sequencing between a camera unit and a CMOS sensor in accordance with the principles and teaching of the disclosure.

In an implementation, shown in FIG. 8, a DAC 808 instead of charge pump may be used. The low speed control could program a configuration register with a digital word (if using a DAC) instead of a push-up/push-down (if using a charge pump).

Figure 9:
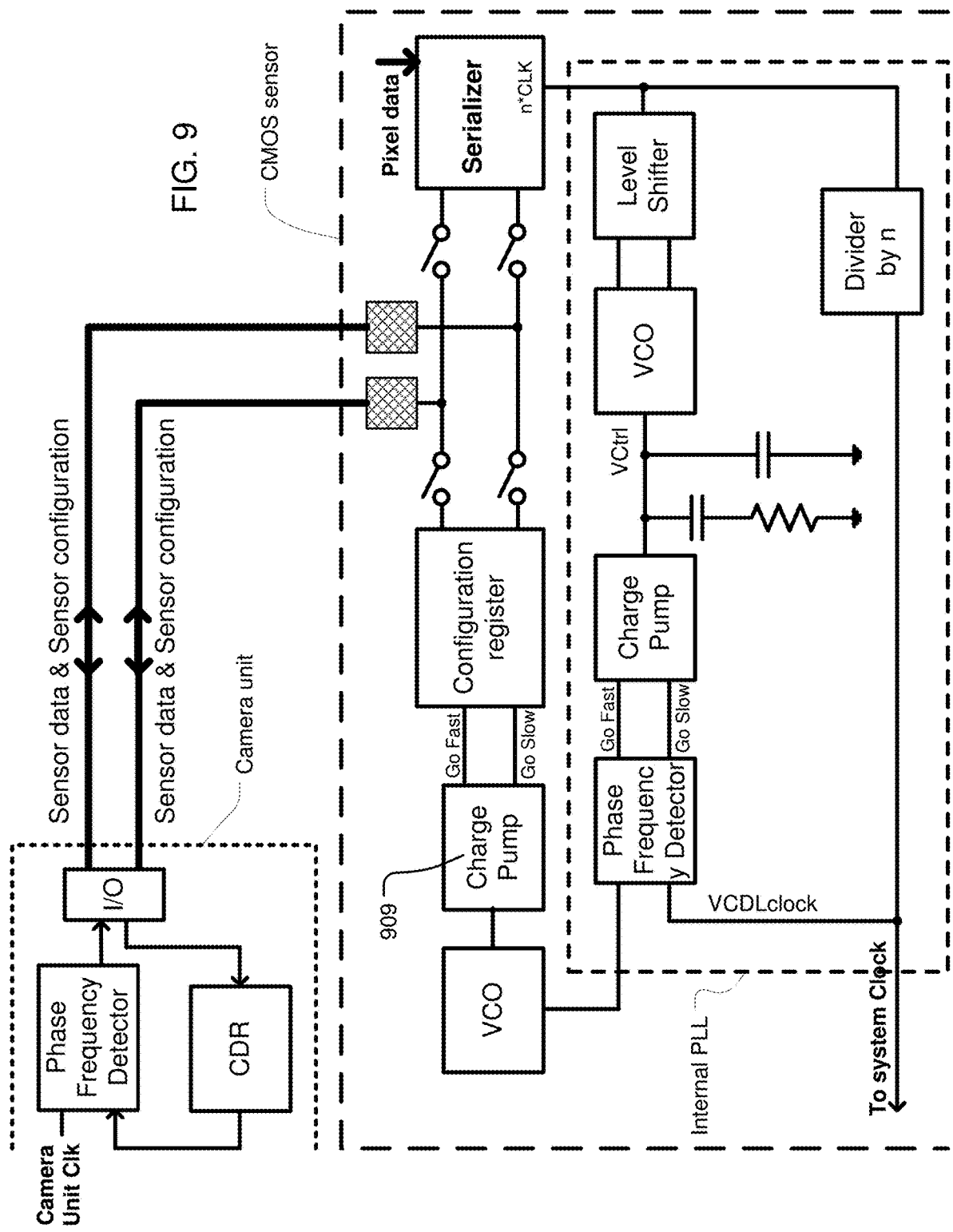
FIG. 9 illustrates a schematic representation of an embodiment of circuitry for clock management and data sequencing between a camera unit and a CMOS sensor in accordance with the principles and teaching of the disclosure.
Figure 10:
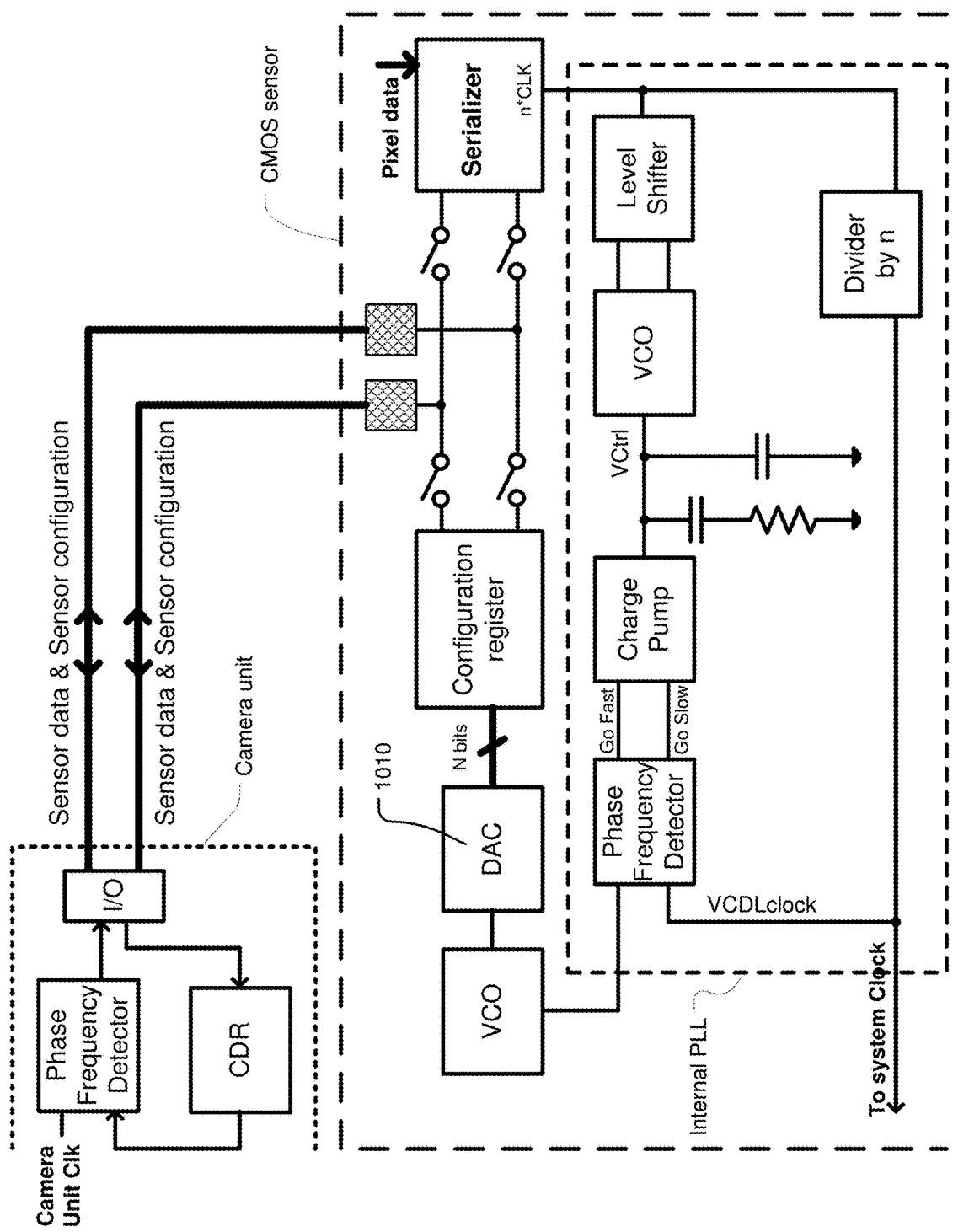
FIG. 10 illustrates a schematic representation of an embodiment of circuitry for clock management and data sequencing between a camera unit and a CMOS sensor in accordance with the principles and teaching of the disclosure.

It may be desirable to build such a system without segmenting the on-chip PLL. The embodiment of FIG. 9 depicts an equivalent circuit where the internal PLL remains unchanged, but the clock input pad is removed and the input clock signal is provided by a clock generator distributed circuit equivalent to that of FIG. 7. The version of this last circuit using a DAC 1010 instead of a charge pump 909 is shown in FIG. 10.

Figure 11:
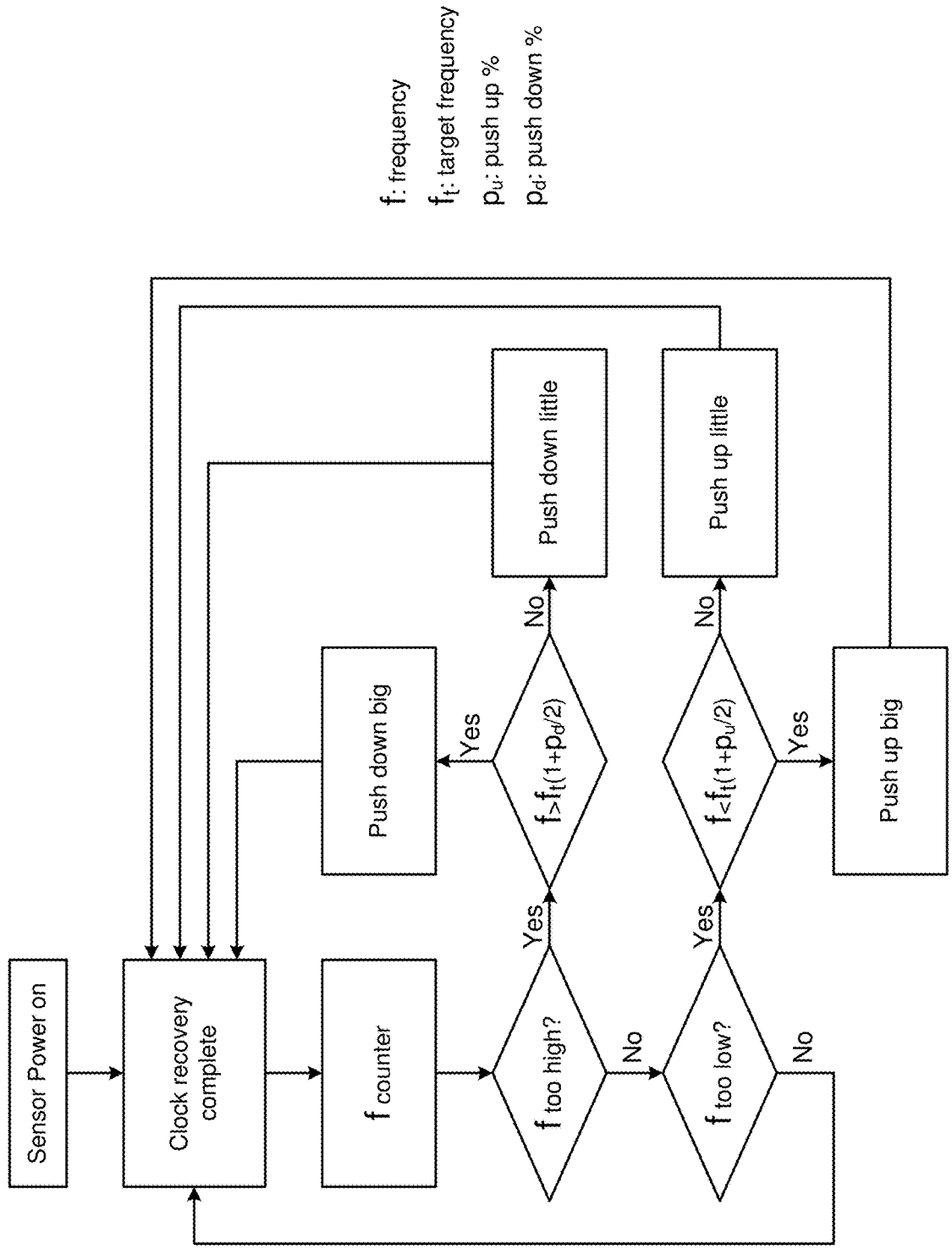
FIG. 11 illustrates a flow chart of an embodiment of the adjustment of a CMOS sensor operating frequency in accordance with the principles and teachings of the disclosure.

In an embodiment, an algorithm that may reside in the camera unit is depicted in FIG. 11, and may be built for a charge pump based system. The Table in FIG. 12 lists the signals and parameters that may be used by the camera unit for the FIG. 11 algorithm.

The following is an example of the algorithm implementation. The R_CLK may be compared to the target frequency using REF_CLK as the method or mode of comparison. If R_CLK is too low then PUSH UP may be asserted. If R_CLK is too high then PUSH DOWN may be asserted. The BIG_LITTLE output may be used based on how far R_CLK is from the target frequency. As an example, if a big push represents a 5% change and a little push represents a 1% change in frequency then if R_CLK is lower than target frequency minus 3%, the block may issue a PUSH UP BIG command. The next time the R_CLK is measured it will be approximately 2% greater than the target and so the block may issue a PUSH DOWN LITTLE command.

The method of comparing the R_CLK to the target frequency may be as follows. In an example, if the REF_CLK is 27 MHz, the target is 40 MHz and the R_CLK is 38 MHz, then the block may count the number of R_CLK transitions over 1 ms (or 27,000 transitions of REF_CLK). It may compare its counter value, now 38,000 to the desired target of 40,000 and issue a PUSH UP BIG command assuming the BIG and LITTLE thresholds are 5% and 1%.

It will be appreciated that implementations of the disclosure may comprise or utilize a special purpose or general-purpose computer including computer hardware, such as, for example, one or more processors and system memory, as discussed in greater detail below. Implementations within the scope of the disclosure may also include physical and other computer-readable media for carrying or storing computer-executable instructions and/or data structures. Such computer-readable media can be any available media that can be accessed by a general purpose or special purpose computer system. Computer-readable media that store computer-executable instructions may be computer storage media (devices). Computer-readable media that carry computer-executable instructions may be transmission media. Thus, by way of example, and not limitation, implementations of the disclosure can comprise at least two distinctly different kinds of computer-readable media: computer storage media (devices) and transmission media.

Computer storage media (devices) includes RAM, ROM, EEPROM, CD-ROM, solid state drives ("SSDs") (e.g., based on RAM), Flash memory, phase-change memory ("PCM"), other types of memory, other optical disk storage, magnetic disk storage or other magnetic storage devices, or any other medium which can be used to store desired program code means in the form of computer-executable instructions or data structures and which can be accessed by a general purpose or special purpose computer.

A "network" may be defined as one or more data links that enable the transport of electronic data between computer systems and/or modules and/or other electronic devices. In an implementation, a sensor and camera control unit may be networked in order to communicate with each other, and other components, connected over the network to which they may be connected. When information is transferred or provided over a network or another communications connection (either hardwired, wireless, or a combination of hardwired or wireless) to a computer, the computer properly views the connection as a transmission medium. Transmissions media can include a network and/or data links which can be used to carry desired program code means in the form of computer-executable instructions or data structures and which can be accessed by a general purpose or special purpose computer. Combinations of the above should also be included within the scope of computer-readable media.

Further, upon reaching various computer system components, program code means in the form of computer-executable instructions or data structures that can be transferred automatically from transmission media to computer storage media (devices) (or vice versa). For example, computer-executable instructions or data structures received over a network or data link can be buffered in RAM within a network interface module (e.g., a "NIC"), and then eventually transferred to computer system RAM and/or to less volatile computer storage media (devices) at a computer system. RAM can also include solid state drives (SSDs or PCIx based real time memory tiered Storage, such as FusionIO). Thus, it should be understood that computer storage media (devices) can be included in computer system components that also (or even primarily) utilize transmission media.

Computer-executable instructions comprise, for example, instructions and data which, when executed at a processor, cause a general purpose computer, special purpose computer, or special purpose processing device to perform a certain function or group of functions. The computer executable instructions may be, for example, binaries, intermediate format instructions such as assembly language, or even source code. Although the subject matter has been described in language specific to structural features and/or methodological acts, it is to be understood that the subject matter defined in the appended disclosure is not necessarily limited to the described features or acts described above. Rather, the described features and acts may be disclosed as example forms of implementing the disclosure.

Those skilled in the art will appreciate that the disclosure may be practiced in network computing environments with many types of computer system configurations, including, personal computers, desktop computers, laptop computers, message processors, control units, camera control units, hand-held devices, hand pieces, multi-processor systems, microprocessor-based or programmable consumer electronics, network PCs, minicomputers, mainframe computers, mobile telephones, PDAs, tablets, pagers, routers, switches, various storage devices, and the like. It should be noted that any of the above mentioned computing devices may be provided by or located within a brick and mortar location. The disclosure may also be practiced in distributed system environments where local and remote computer systems, which may be linked (either by hardwired data links, wireless data links, or by a combination of hardwired and wireless data links) through a network, both perform tasks. In a distributed system environment, program modules may be located in both local and remote memory storage devices.

Further, where appropriate, functions described herein can be performed in one or more of: hardware, software, firmware, digital components, or analog components. For example, one or more application specific integrated circuits (ASICs) or field programmable gate arrays can be programmed to carry out one or more of the systems and procedures described herein. Certain terms may be used throughout the following description and Disclosure to refer to particular system components. As one skilled in the art will appreciate, components may be referred to by different names. This document does not intend to distinguish between components that differ in name, but not function.

Figure 13:
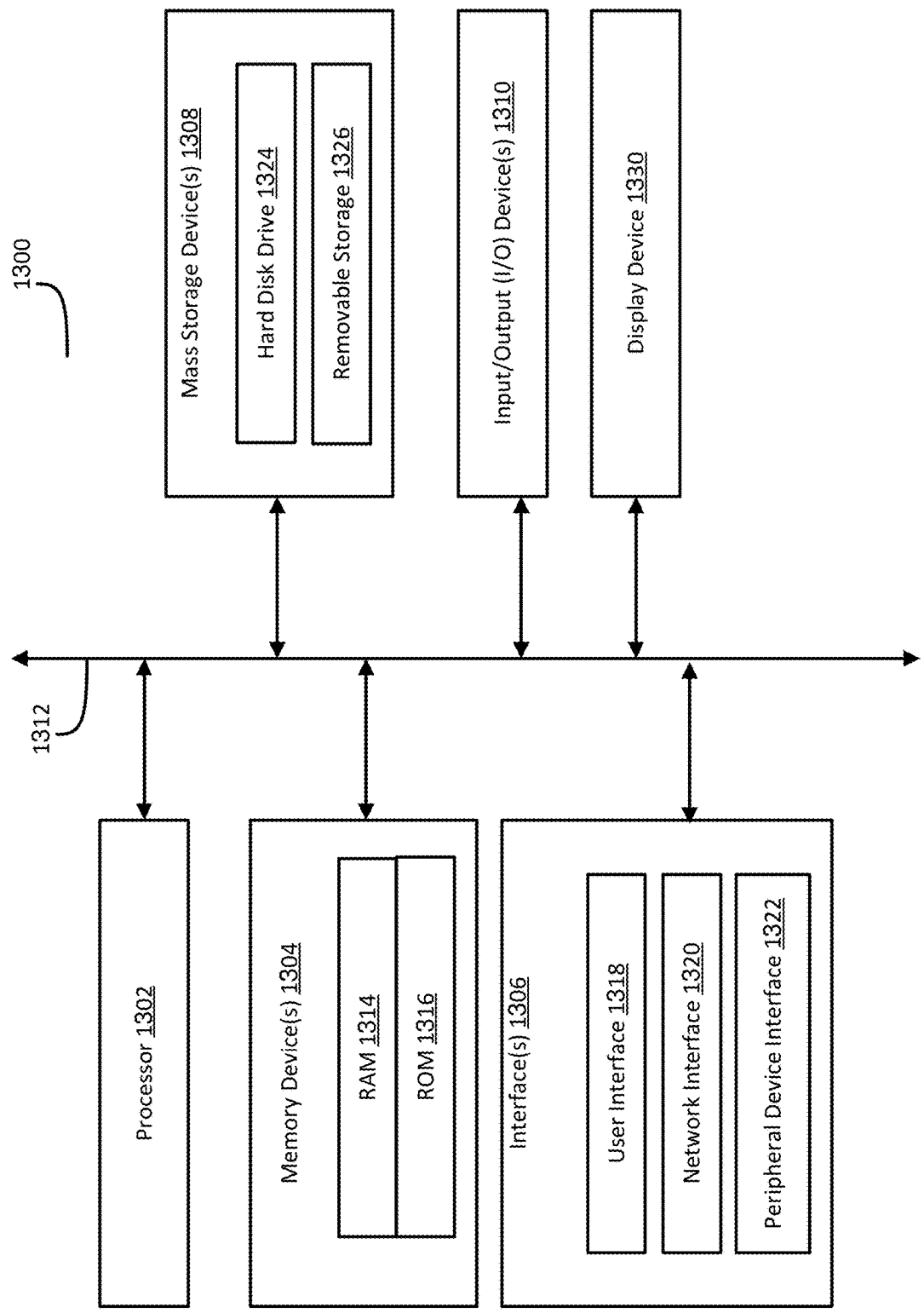
FIG. 13 illustrates an embodiment of hardware in accordance with the principles and teachings of the disclosure.

FIG. 13 is a block diagram illustrating an example computing device 1300. Computing device 1300 may be used to perform various procedures, such as those discussed herein. Computing device 1300 can function as a server, a client, or any other computing entity. Computing device can perform various monitoring functions as discussed herein, and can execute one or more application programs, such as the application programs described herein. Computing device 1300 can be any of a wide variety of computing devices, such as a desktop computer, a notebook computer, a server computer, a handheld computer, camera control unit, tablet computer and the like.

Computing device 1300 includes one or more processor(s) 1302, one or more memory device(s) 1304, one or more interface(s) 1306, one or more mass storage device(s) 1308, one or more Input/Output (I/O) device(s) 1310, and a display device 1330 all of which may be coupled to a bus 1312. Processor(s) 1302 include one or more processors or controllers that execute instructions stored in memory device(s) 1304 and/or mass storage device(s) 1308. Processor(s) 1302 may also include various types of computer-readable media, such as cache memory.

Memory device(s) 1304 include various computer-readable media, such as volatile memory (e.g., random access memory (RAM) 1314) and/or nonvolatile memory (e.g., read-only memory (ROM) 1316). Memory device(s) 1304 may also include rewritable ROM, such as Flash memory.

Mass storage device(s) 1308 include various computer readable media, such as magnetic tapes, magnetic disks, optical disks, solid-state memory (e.g., Flash memory), and so forth. As shown in FIG. 13, a particular mass storage device is a hard disk drive 1324. Various drives may also be included in mass storage device(s) 1308 to enable reading from and/or writing to the various computer readable media. Mass storage device(s) 1308 include removable media 1326 and/or non-removable media.

I/O device(s) 1310 include various devices that allow data and/or other information to be input to or retrieved from computing device 1300. Example I/O device(s) 1310 include digital imaging devices, electromagnetic sensors and emitters, cursor control devices, keyboards, keypads, microphones, monitors or other display devices, speakers, printers, network interface cards, modems, lenses, CCDs or other image capture devices, and the like.

Display device 1330 includes any type of device capable of displaying information to one or more users of computing device 1300. Examples of display device 1330 include a monitor, display terminal, video projection device, and the like.

Interface(s) 1306 include various interfaces that allow computing device 1300 to interact with other systems, devices, or computing environments. Example interface(s) 1306 may include any number of different network interfaces 1320, such as interfaces to local area networks (LANs), wide area networks (WANs), wireless networks, and the Internet. Other interface(s) include user interface 1318 and peripheral device interface 1322. The interface(s) 1306 may also include one or more user interface elements 1318. The interface(s) 1306 may also include one or more peripheral interfaces such as interfaces for printers, pointing devices (mice, track pad, etc.), keyboards, and the like.

Bus 1312 allows processor(s) 1302, memory device(s) 1304, interface(s) 1306, mass storage device(s) 1308, and I/O device(s) 1310 to communicate with one another, as well as other devices or components coupled to bus 1312. Bus 1312 represents one or more of several types of bus structures, such as a system bus, PCI bus, IEEE 1394 bus, USB bus, and so forth.

For purposes of illustration, programs and other executable program components may be shown herein as discrete blocks, although it is understood that such programs and components may reside at various times in different storage components of computing device 1300, and may be executed by processor(s) 1302. Alternatively, the systems and procedures described herein can be implemented in hardware, or a combination of hardware, software, and/or firmware. For example, one or more application specific integrated circuits (ASICs) can be programmed to carry out one or more of the systems and procedures described herein.

It will be appreciated that the disclosure may be used with any image sensor, whether a CMOS image sensor or CCD image sensor, without departing from the scope of the disclosure. Further, the image sensor may be located in any location within the overall system, including, but not limited to, the tip of the endoscope, the hand piece of the imaging device or camera, the control unit, or any other location within the system without departing from the scope of the disclosure.

Implementations of an image sensor that may be utilized by the disclosure include, but are not limited to, the following, which are merely examples of various types of sensors that may be utilized by the disclosure.

Figure 14A:
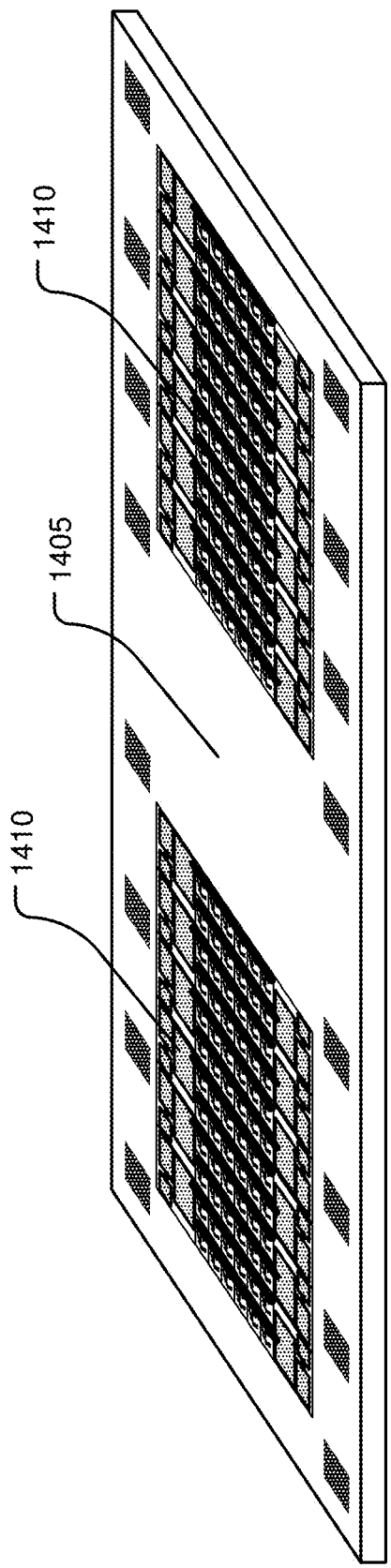
FIGS. 14A and 14B illustrate an embodiment of a sensor having a plurality of pixel arrays for providing three dimensional functionality in accordance with the principles and teachings of the disclosure.
Figure 14B:
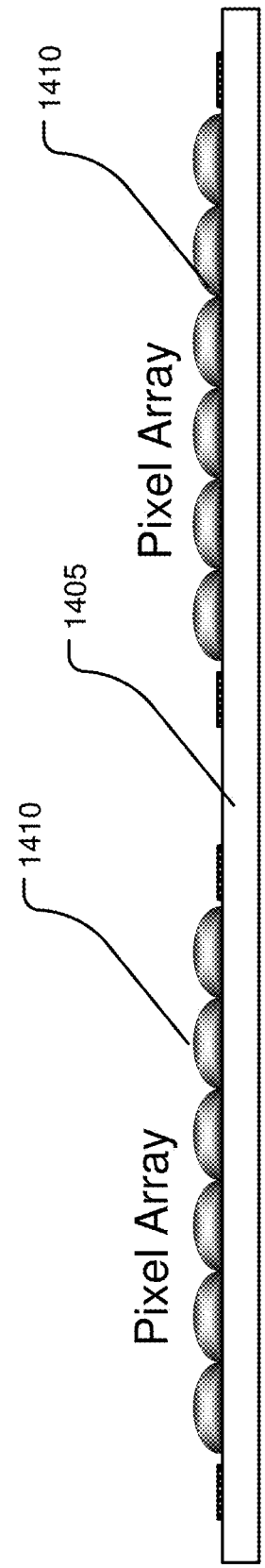

FIGS. 14A and 14B illustrate an implementation of a monolithic sensor 1405 having a plurality of pixel arrays 1410 for producing a three dimensional image in accordance with the teachings and principles of the disclosure. Such an implementation may be desirable for three dimensional image capture, wherein the two pixel arrays 1410 may be offset during use. In another implementation, a first pixel array 1410 and a second pixel array 1410 may be dedicated to receiving a predetermined range of wave lengths of electromagnetic radiation, wherein the first pixel array 1410 is dedicated to a different range of wave length electromagnetic radiation than the second pixel array 1410.

Figure 15A:
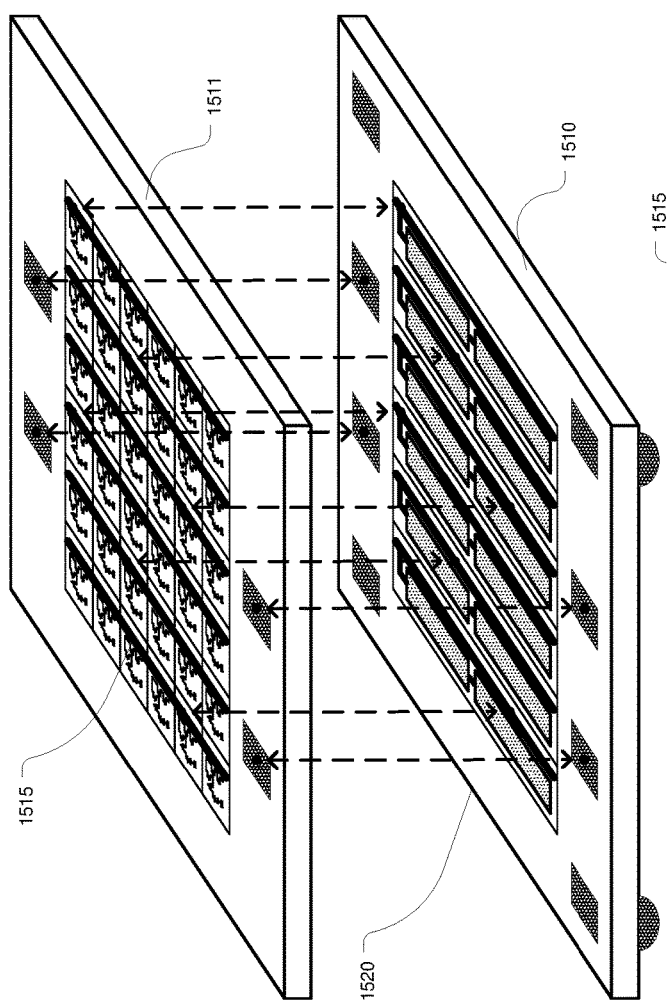
FIGS. 15A and 15B illustrate a view of an implementation of an imaging sensor built on a plurality of substrates, wherein a plurality of pixel columns forming the pixel array are located on the first substrate and a plurality of circuit columns may be located on a second substrate and showing an electrical connection and communication between one column of pixels to its associated or corresponding column of circuitry.
Figure 15B:
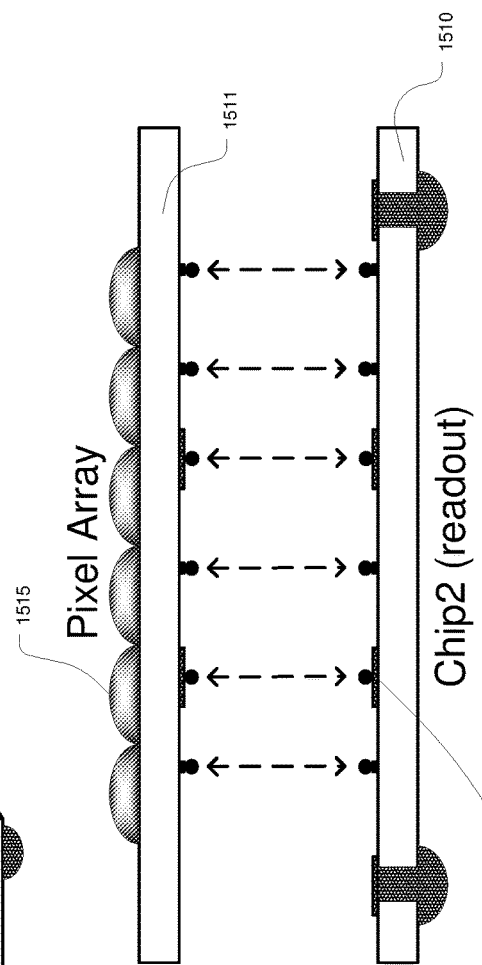

FIGS. 15A and 15B illustrate a view of an implementation of an imaging sensor built on a plurality of substrates 1510, 1511. As illustrated, a plurality of pixel columns forming the pixel array 1515 are located on the first substrate 1511 and a plurality of circuit columns 1520 are located on a second substrate 1510. Also illustrated in the figure are the electrical connection and communication between one column of pixels to its associated or corresponding column of circuitry.

In one implementation, an image sensor, which might otherwise be manufactured with its pixel array and supporting circuitry on a single, monolithic substrate/chip, may have the pixel array separated from all or a majority of the supporting circuitry. The disclosure may use at least two substrates/chips, which will be stacked together using three-dimensional stacking technology. The first of the two substrates/chips may be processed using an image CMOS process. The first substrate/chip may be comprised either of a pixel array exclusively or a pixel array surrounded by limited circuitry. The second or subsequent substrate/chip may be processed using any process, and does not have to be from an image CMOS process. The second substrate/chip may be, but is not limited to, a highly dense digital process in order to integrate a variety and number of functions in a very limited space or area on the substrate/chip, or a mixed-mode or analog process in order to integrate for example precise analog functions, or a RF process in order to implement wireless capability, or MEMS (Micro-Electro-Mechanical Systems) in order to integrate MEMS devices. The image CMOS substrate/chip may be stacked with the second or subsequent substrate/chip using any three-dimensional technique. The second substrate/chip may support most, or a majority, of the circuitry that would have otherwise been implemented in the first image CMOS chip (if implemented on a monolithic substrate/chip) as peripheral circuits and therefore have increased the overall system area while keeping the pixel array size constant and optimized to the fullest extent possible. The electrical connection between the two substrates/chips may be done through interconnects, which may be wirebonds, bump and/or TSV (Through Silicon Via).

Figure 16A:
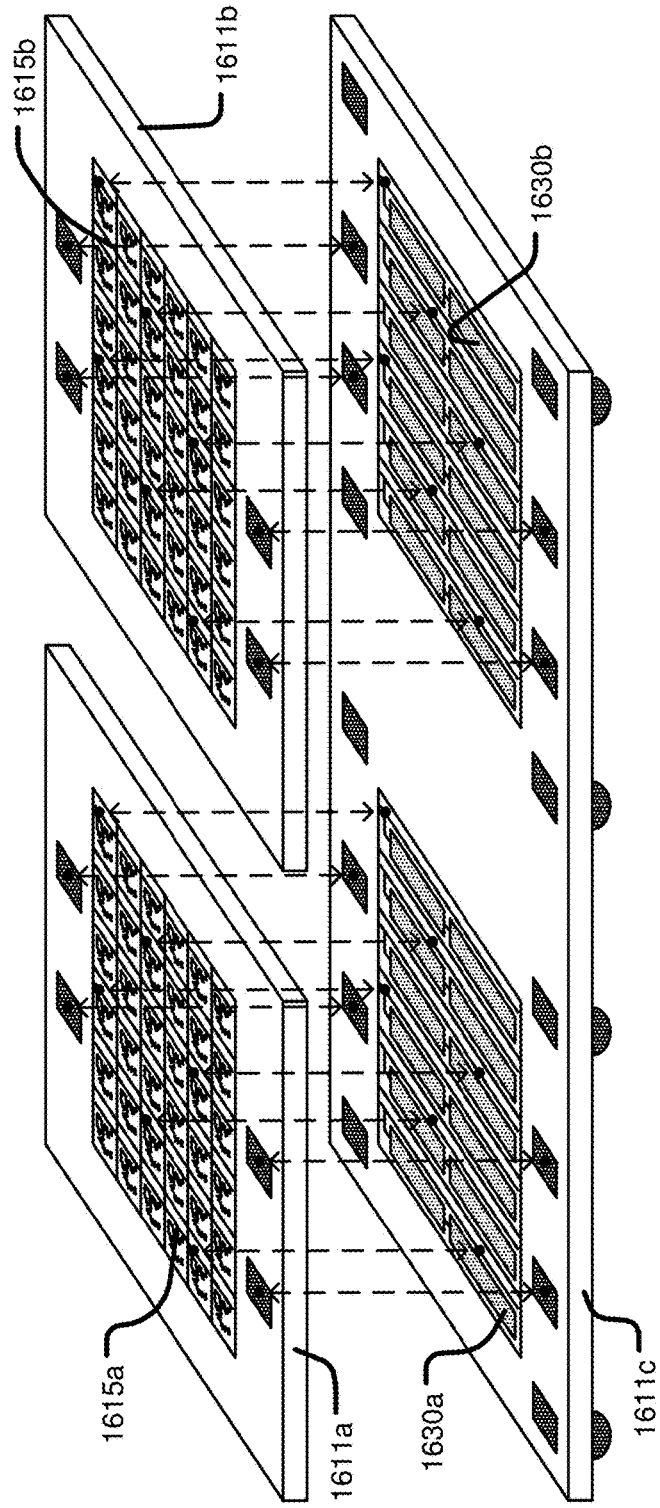
FIGS. 16A and 16B illustrate a view of an implementation of an imaging sensor having a plurality of pixel arrays for producing a three dimensional image, wherein the plurality of pixel arrays and the image sensor may be built on a plurality of substrates.
Figure 16B:
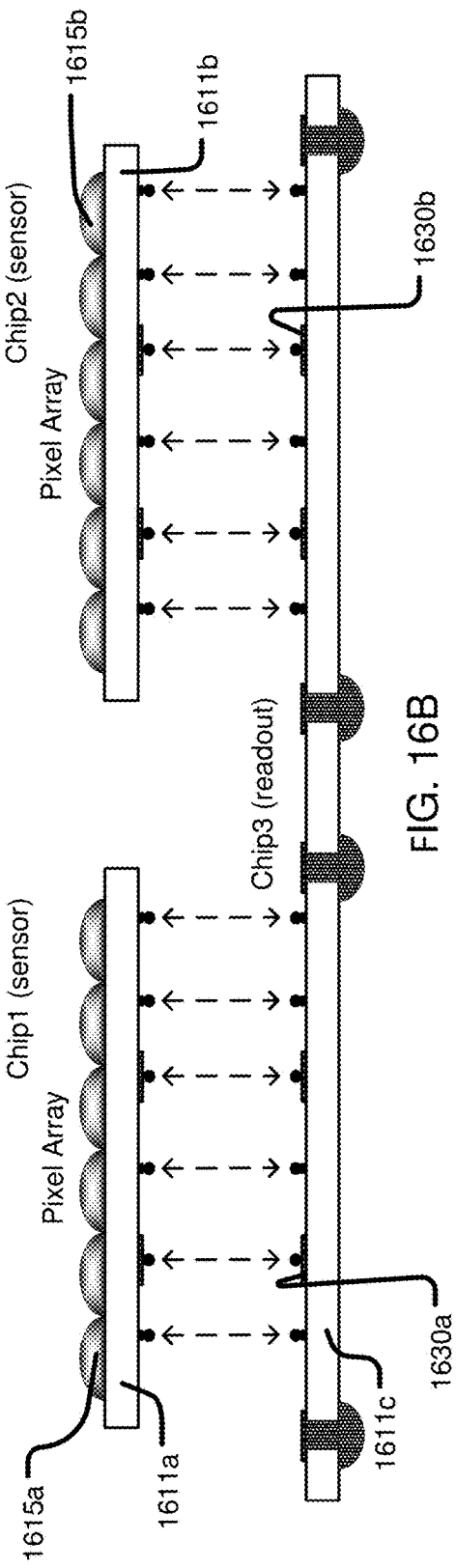

FIGS. 16A and 16B illustrate a view of an implementation of an imaging sensor having a plurality of pixel arrays for producing a three dimensional image. The three dimensional image sensor may be built on a plurality of substrates 1611a, 1611b, 1611c, and may comprise the plurality of pixel arrays 1615a, 1615b and other associated circuitry 1630a, 1630b, wherein a plurality of pixel columns forming the first pixel array and a plurality of pixel columns forming a second pixel array are located on respective substrates and a plurality of circuit columns are located on a separate substrate. Also illustrated are the electrical connections and communications between columns of pixels to associated or corresponding column of circuitry.

It will be appreciated that the teachings and principles of the disclosure may be used in a reusable device platform, a limited use device platform, a re-posable use device platform, or a single-use/disposable device platform without departing from the scope of the disclosure. It will be appreciated that in a re-usable device platform an end-user is responsible for cleaning and sterilization of the device. In a limited use device platform the device can be used for some specified amount of times before becoming inoperable. Typical new device is delivered sterile with additional uses requiring the end-user to clean and sterilize before additional uses. In a re-posable use device platform a third-party may reprocess the device (e.g., cleans, packages and sterilizes) a single-use device for additional uses at a lower cost than a new unit. In a single-use/disposable device platform a device is provided sterile to the operating room and used only once before being disposed of.

Additionally, the teachings and principles of the disclosure may include any and all wavelengths of electromagnetic energy, including the visible and non-visible spectrums, such as infrared (IR), ultraviolet (UV), and X-ray.

It will be appreciated that various features disclosed herein provide significant advantages and advancements in the art. The following embodiments may be exemplary of some of those features.

An embodiment of a reduced area image sensor may comprise: input and output pads wherein the pad count is reduced by no having a no synchronization clock pad; wherein signal transitions are encoded within the output data; service lines within the frame; wherein a camera unit clock and/or data recovery circuit may be used to lock on the incoming sensor data to keep it synchronized. An embodiment may further comprise a minimal area CMOS image sensor disposed within the distal end of endoscopes. An embodiment may further comprise at least one transition within each pixel serial data created within the pixel array. An embodiment may further comprise at least one transition during a series of a plurality pixel data sets created by the pixel array. An embodiment may further comprise a plurality of transitions within each pixel serial data created by the pixel array. An embodiment may further comprise replaced pixel data with clock signal data. An embodiment may further comprise replaced pixel data with clock signal data within at least one service line phase of one frame period. An embodiment may further comprise replaced pixel data with clock signal data within the service line phase just prior to the true pixel data output phase. An embodiment may further comprise replaced pixel data with clock signal data within and at all output frame phases except during pixel data output phase.

An embodiment of a reduced image sensor may operate, be designed by, and may comprise: replacing pixel data with clock signal data within, and at all output frame phases including during pixel data output phase; removing clock pads; building a Phase Lock Loop (PLL) with blocks of the sensor and other blocks of the camera unit; using data lines and configuration lines for connecting together sensor PLL blocks and camera unit PLL blocks; and using the camera unit clock and data recovery circuit to lock on the incoming sensor data. An embodiment may further comprise minimal area CMOS image sensor for use in the distal end of endoscopes. An embodiment may further comprise bidirectional data pads to issue image data during a defined portion of the frame timing. An embodiment may further issue other types of data during another portions of the frame data output. An embodiment may switch direction and receive commands from the external camera system during a third defined time period during the frame while in receive mode. An embodiment may be PLL based on a charge pump for driving the Voltage Controlled Oscillator (VCO). An embodiment may be PLL based on a Digital to Analog Convertor (DAC) for driving the VCO. An embodiment may further comprise programming a sensor configuration register to store increase of decrease of the resultant operating frequency. An embodiment may further comprise local oscillator as a PLL reference clock. An embodiment may further comprise the use differing strength pushes.

In the foregoing Detailed Description of the Disclosure, various features of the disclosure may be grouped together in a single embodiment for the purpose of streamlining the disclosure. This method of disclosure is not to be interpreted as reflecting an intention that the disclosure requires more features than may be expressly recited in the disclosure. Rather, inventive aspects lie in less than all features of a single foregoing disclosed embodiment.

It is to be understood that the above-described arrangements may be only illustrative of the application of the principles of the disclosure. Numerous modifications and alternative arrangements may be devised by those skilled in the art without departing from the spirit and scope of the disclosure and the appended disclosure may be intended to cover such modifications and arrangements.

Thus, while the disclosure has been shown in the drawings and described above with particularity and detail, it will be apparent to those of ordinary skill in the art that numerous modifications, including, but not limited to, variations in size, materials, shape, form, function and manner of operation, assembly and use may be made without departing from the principles and concepts set forth herein.

Further, where appropriate, functions described herein can be performed in one or more of: hardware, software, firmware, digital components, or analog components. For example, one or more application specific integrated circuits (ASICs) can be programmed to carry out one or more of the systems and procedures described herein. Certain terms may be used throughout the following description and Disclosure to refer to particular system components. As one skilled in the art will appreciate, components may be referred to by different names. This document does not intend to distinguish between components that differ in name, but not function.

The foregoing description has been presented for the purposes of illustration and description. It is not intended to be exhaustive or to limit the disclosure to the precise form disclosed. Many modifications and variations may be possible in light of the above teaching. Further, it should be noted that any or all of the aforementioned alternate implementations may be used in any combination desired to form additional hybrid implementations of the disclosure.

Further, although specific implementations of the disclosure have been described and illustrated, the disclosure is not to be limited to the specific forms or arrangements of parts so described and illustrated. The scope of the disclosure is to be defined by the disclosure appended hereto, any future disclosure submitted here and in different applications, and their equivalents.

What is claimed is:

1. An endoscopic system for use in a light deficient environment comprising:
   an endoscope comprising an image sensor located at a distal end of the endoscope;
   a control circuit in electronic communication with the image sensor;
   wherein the image sensor comprises:
      a plurality of bidirectional data pads wherein there is no dedicated input synchronization clock pad, such that a number of bidirectional pads is reduced thereby reducing an area of the image sensor;
      wherein electronic communication through each of the bidirectional pads is performed in three defined phases of a frame period:
         a rolling-readout phase during which image data is output from the image sensor through the bidirectional pads to the control circuit,
         a service-line phase during which non-image data is output from the image sensor through the bidirectional pads to the control circuit, and a configuration phase during which image sensor configuration data is received by the image sensor from the control circuit through the bidirectional pads, wherein signal transitions are encoded within pixel data that is output from the image sensor in correspondence to the defined phases of the bidirectional pads by adding an additional bit to the pixel data, where the additional bit is an inverted version of a specified bit out of a plurality of bits in the pixel data.

2. The endoscopic system of claim 1, wherein the output data comprises signal transitions as service lines within frame data.

3. The endoscopic system of claim 1, wherein a camera unit clock is used to synchronize incoming sensor data.

4. The endoscopic system of claim 1, wherein a data recovery circuit is used to lock on incoming sensor data to keep it synchronized.

5. The endoscopic system of claim 1, further comprising at least one transition within each of a plurality of pixel data values created within a pixel array of the image sensor.

6. The endoscopic system of claim 5, further comprising at least one transition during a series of the plurality of pixel data values created by the pixel array.

7. The endoscopic system of claim 5, further comprising a plurality of transitions within each of the plurality of pixel data values created by the pixel array.

8. The endoscopic system of claim 1, wherein pixel data in at least one pixel data value is replaced with clock signal data for synchronization.

9. The endoscopic system of claim 1, wherein pixel data in at least one pixel data value is replaced with clock signal data within at least one service line phase of one frame period.

10. The endoscopic system of claim 1, wherein pixel data in at least one pixel data value is replaced with clock signal data within the service line phase just prior to the rolling-readout phase.

11. The endoscopic system of claim 1, wherein clock signal data is transmitted during all frame period phases except during the rolling-readout phase.

12. The endoscopic system of claim 1, further comprising a Phase Lock Loop built with blocks of the image sensor and blocks of the camera unit.

13. The endoscopic system of claim 12, further comprising data lines and configuration lines electrically connecting together image sensor Phase Lock Loop blocks and camera unit Phase Lock Loop blocks.

14. The endoscopic system of claim 13, wherein a camera unit clock and a data recovery circuit are used to lock on to incoming sensor data.

15. The endoscopic system of claim 1, further comprising bidirectional data pads to issue image data during a defined portion of the frame timing.

16. The endoscopic system of claim 15, wherein the data pads issue a plurality of types of data during and corresponding to a plurality of portions of frame data output.

17. The endoscopic system of claim 16, wherein the data pads are configured to switch direction and receive commands from external system components during the configuration phase of the frame period while in receive mode.

18. The endoscopic system of claim 1, further comprising a Phase Loop Lock based on a charge pump for driving a Voltage Controlled Oscillator.

19. The endoscopic system of claim 18, further comprising Phase Loop Lock based on a Digital to Analog Convertor for driving the Voltage Controlled Oscillator.

20. The endoscopic system of claim 1, further comprising a sensor configuration register to store changes in resultant operating frequency.

21. The endoscopic system of claim 1, further comprising a local oscillator as a Phase Lock Loop reference clock.

22. The endoscopic system of claim 1, wherein the plurality of bits representing the pixel data value include a most significant bit and a least significant bit.

23. The endoscopic system of claim 22, wherein the most significant bit is transmitted first and the least significant bit is transmitted last.

24. The endoscopic system of claim 23, wherein the additional bit is added after the least significant bit and is an inverted version of the least significant bit.

* * * * *